United States Patent
Meuillet et al.

(10) Patent No.: US 11,432,547 B2
(45) Date of Patent: Sep. 6, 2022

(54) INHIBITORS OF GRB2-ASSOCIATED BINDING PROTEIN 1 (GAB1) AND METHODS OF TREATING CANCER USING THE SAME

(71) Applicants: Arizona Board of Regents on Behalf of the University of Arizona, Tucson, AZ (US); Board of Regents, The University of Texas System, Austin, TX (US)

(72) Inventors: Emmanuelle J. Meuillet, Tucson, AZ (US); Shuxing Zhang, Houston, TX (US); Lu Chen, Houston, TX (US)

(73) Assignees: Arizona Board of Regents on Behalf of the University of Arizona, Tucson, AZ (US); Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/598,742

(22) Filed: Oct. 10, 2019

(65) Prior Publication Data
US 2020/0396995 A1  Dec. 24, 2020

Related U.S. Application Data

(62) Division of application No. 15/516,664, filed as application No. PCT/US2015/054027 on Oct. 5, 2015, now Pat. No. 10,448,637.

(60) Provisional application No. 62/059,330, filed on Oct. 3, 2014.

(51) Int. Cl.
| | |
|---|---|
| C07D 417/14 | (2006.01) |
| A01N 41/10 | (2006.01) |
| C07D 413/14 | (2006.01) |
| C07D 233/84 | (2006.01) |
| C07D 405/06 | (2006.01) |
| C07D 409/04 | (2006.01) |
| C07D 409/06 | (2006.01) |
| C07D 413/12 | (2006.01) |
| C07D 417/04 | (2006.01) |
| C07D 487/04 | (2006.01) |
| C07D 285/135 | (2006.01) |
| C07D 213/83 | (2006.01) |
| A61K 31/10 | (2006.01) |
| A61K 31/00 | (2006.01) |

(52) U.S. Cl.
CPC ............ *A01N 41/10* (2013.01); *A61K 31/10* (2013.01); *C07D 213/83* (2013.01); *C07D 233/84* (2013.01); *C07D 285/135* (2013.01); *C07D 405/06* (2013.01); *C07D 409/04* (2013.01); *C07D 409/06* (2013.01); *C07D 413/12* (2013.01); *C07D 413/14* (2013.01); *C07D 417/04* (2013.01); *C07D 417/14* (2013.01); *C07D 487/04* (2013.01); *A61K 31/00* (2013.01)

(58) Field of Classification Search
CPC .................................................. C07D 417/14
See application file for complete search history.

(56) References Cited

U.S. PATENT DOCUMENTS

| | | | |
|---|---|---|---|
| 8,420,678 B2 | 4/2013 | Mahadevan et al. | |
| 8,628,961 B2 | 1/2014 | Degterev et al. | |
| 10,448,637 B2 * | 10/2019 | Meuillet | C07D 417/14 |
| 2005/0215548 A1 | 9/2005 | Wang et al. | |
| 2013/0184317 A1 | 7/2013 | Mahadevan et al. | |

FOREIGN PATENT DOCUMENTS

| | | | |
|---|---|---|---|
| WO | WO-2010026365 | 3/2010 | |
| WO | WO-2010026365 A1 * | 3/2010 | C07D 471/04 |
| WO | WO-2011032169 A2 | 3/2011 | |

OTHER PUBLICATIONS

E.J. Meuillet et al., "Molecular Pharmacology and Antitumor Activity of PHT-427, a Novel AKt/Phosphatidylinositide-Dependent Protein Kinase 1 Pleckstrin Homology Domain Inhibitor." Mol. Cancer Ther, vol. 9, No. 3, pp. 706-717, Mar. 2010.
American Cancer Soc., Breast Cancer Rish and Prevention, 2018, Available from https://www.cancer.org/cancer/breast-cancer/risk-and-prevention.html.
Mayo Clinic, Lung Cancer, 2018, Available from <https://www.mayoclinic.org/disease-conditions/lung-cancer/symptoms-causes/syc-20374620>.
Padilla, C.O., et al., Functional Characterization of Cancer-associated Gab1 Mutations, Oncogene, 2013, 32:2696-2702.

* cited by examiner

*Primary Examiner* — John S Kenyon
(74) *Attorney, Agent, or Firm* — Blank Rome LLP

(57) ABSTRACT

Identification and evaluation of a set of first-in-class potent inhibitors targeting a new cancer target, Grb2-associated binder-1 (GAB1), which integrates signals from different signaling pathways and is frequently over-expressed in cancer cells. Intensive computational modeling is utilized to understand the structure of the GAB1 pleckstrin homology (PH) domain and screened five million compounds. Upon biological evaluation, several inhibitors were found that induced large conformational changes of the target structure exhibited strong selective binding to GAB1 PH domain. Particularly, these inhibitors demonstrated potent and tumor-specific cytotoxicity in breast cancer cells. This targeting GAB1 signaling may be used for cancer therapy, especially for triple negative breast cancer patients.

4 Claims, 20 Drawing Sheets
Specification includes a Sequence Listing.

FIG. 2

```
          *:   :              ; *;* *           : *:;.:              :
GAB1  EVV GGWLN F -EKELARYAN  RFVLPSGRLTGD DVLE YY DHA-----KK IR ILD
1QQG  DVRKVGYLP           K       PRFFVLPAASEAGG AKLE YE EKKWPHRSSA    I
1EA2  AVIKAGY  V  G-AV K----   K YFQLDE-------NTIGF   ELE-----KE  LV I
3TFM  EALKQGWLP NGGGSSTLSPR   K WFVLRQ--------SKL  FENDSE------EKL G VE
1FRO  LGT  GYL  QGG---LVK--TW    FTLHR--------NRLK   DQ S------PR IK ILD
         ββββββ             ββββββββ         βββββ               ββββ

:     :                  . ;    .* : *.;  :     .*    ?
GAB1  LNL QQVDAGL FNKKEPENS YIPDINTID  IFYLVASGEE   KKWVP  I  DI G---
1QQG  LE   F INNP------ADEENK LVALY TRDE FAYAADS EARQDSNYQALLQLE----
1EA2  LKEV KVQE ---KQGDI   KD LFEIVT G  FYVQADS  EE   GWIKAVGGAIVAQ
3TFM  VREAKEILD TNK-------ENGIDII ADN FR LIAES  EDAS QWFSVLSQV S---
1FRO  LTE SAVQ FD--YS----QEPV     LVFF  TFYL AK GVEADE I ILN KLSQ-
          βββββ          βββββ      ββββββ    αααααααααααααααα
```

INHIBITORS OF GRB2-ASSOCIATED BINDING PROTEIN 1 (GAB1) AND METHODS OF TREATING CANCER USING THE SAME

CROSS REFERENCE

This application is a divisional of U.S. patent application Ser. No. 15/516,664, filed Apr. 3, 2017, which is the U.S. national stage of International Patent Application No. PCT/US2015/054027, filed Oct. 5, 2015, which claims priority to U.S. Provisional Patent Application No. 62/059,330, filed Oct. 3, 2014, each of which is incorporated herein in its entirety by reference.

FIELD OF THE INVENTION

The present invention relates to compounds that inhibit Grb2-associated binder-1 (GAB1) and methods of utilizing said compounds to treat cancer, in particular, breast cancer. Moreover, the present invention features a unique method constructing pleckstrin homology (PH) domain structure models and targeting them for drug discovery.

BACKGROUND OF THE INVENTION

Overexpression of Grb2-associated binding protein 1 (GAB1) has been observed in several human cancers, such as breast and lung cancers. This protein is a substrate of several growth factors and interleukin receptors, and it is involved in the integration of different signal transductions. Particularly, GAB1 mediates the activation of mitogen-activated protein kinase (MAPK) and phosphoinositide 3-kinase (PI-3K) cascades. It belongs to a family of scaffolding proteins closely related to the insulin receptor substrates (e.g., IRS1). It contains an N-terminal pleckstrin homology (PH) domain binding to phosphatidylinositol-(3,4,5)-triphosphate (PtdIns(3,4,5)$P_3$), tyrosine phosphorylation sites for the Src homology 2 (SH2) binding and a proline-rich domain interacting with Src homology 3 (SH3) domain. PH domains can be PtdIns subdivided into four groups based on their selective binding to phosphoinositides, and GAB1 PH domain belongs to Group 1 which exhibits the strongest binding to PtdIns(3,4,5)$P_3$, but weak affinity and specificity to PtdIns(3,4)$P_2$ or PtdIns(4,5)$P_2$. Additionally, the phosphorylation of GAB1 on Y627 depends on the intracellular translocation from cytosol to membrane by binding to PtdIns(3,4,5)$P_3$ via its PH domain. Therefore, inhibition of GAB1 PH domain functions may prevent the recruitment of GAB1 to the membrane and suppress cancer cell (e.g., breast cancer) proliferation and metastasis. Herein, the inventors have identified novel small molecule inhibitors that selectively target the PH domain of GAB1, and that exhibit high therapeutic potency for cancer treatment.

Unfortunately, no three-dimensional (3D) structure is available to date for GAB1 PH domain or any PH domain in complex with drug-like small molecules. Challenges remain for accurate structural prediction due to its low sequence identity (<30%) to other PH domains with known structures. However, the core n-sandwich fold among PH domains is conserved, making it possible to construct a reliable homology model structure of GAB1 PH domain. Here, based on the position-site specific matrixes (PSSM) obtained from all non-redundant PH domain structures, the inventors performed fold recognition and homology modeling, followed by intensive structural refinement. The resulted model was then applied to high-throughput virtual screening of a unique collection of over five million drug and lead-like compounds with an in-house drug discovery workflow (FIG. 1). Upon biological evaluation, five out of the initially tested 20 hits exhibited positive activities to form direct binding to GAB1 PH domain, inhibit GAB1 Y627 phosphorylation and suppress breast cancer cell proliferation with low micromolar $IC_{50}$. As is known, triple negative breast cancers are more aggressive with poor prognosis and difficult to treat clinically, but the inhibitors showed high potency against these malicious cells. Therefore, this present invention validates the effectiveness of the in silico platform for drug discovery, and demonstrates that targeting the PH domain of GAB1 provides a promising and novel therapeutic strategy for cancer treatment.

Outside of biological treatments, there are other ways to treat cancer. These include: surgery, chemotherapy, and radiation therapy. Surgery is usually only used in cancer that is isolated in one place and not metastasized cancer. Chemotherapy has ill side-effects due to it targeting many fast growing cells. Radiation therapy has the potential to kill even non harmful cells. Within biological treatments, there are four main categories. The first is rituximab, which can target antigens on cancerous cells which in turn can signal antigens on B-cells. These B-cells can then lyse the cancerous cells. One major advantage that the present invention has over these types of therapies is versatility. In order to target specific antigens, the drug must be specifically made to do this. Antigens differ from cell to cell, so different drugs have to be made to target different cell types.

Another type of treatment involves removing the immune system's inability to attack the body's own cells. Drugs such as ipillimumab can allow immune cells to attack body tissue. This opens up a large possibility of immune cells attacking tissue that is not cancerous or harmful. Therefore, a variety of autoimmune issues may emerge from this treatment path. A third type of biological cancer treatment involves attaching a cell-killing substance onto an antibody. When the antibody binds onto a cancerous cell antigen, the cancer cell with intake the cell-killing substance, and promptly undergoes cell death. Again, there is the chance that non-cancerous cells may uptake this substance and undergo apoptosis. Lastly, there exist the inhibitory biological compounds similar to the present invention. In addition to inhibiting GAB1, there are compounds which inhibit other molecules like growth effectors such as cetuximab and panitumumab. Unlike the present invention, these treatments are usually specific to cancer that is caused by a mutation in the KRAS gene.

In the present invention, the compounds may be used as a cancer therapeutic drug. Some advantages of the present invention are that the compound works upstream of other chemical components, the compounds do not directly target components of the immune system, and this biological inhibitor-based treatment has less damaging side effects than radiation or chemotherapy. There are a few call signaling pathways that are heavily involved in the pathogenesis of cancer. Two of these pathways are the RAS pathway and the PI3K pathway, and both of these pathways are deregulated in the formation of human cancer thereby leading to the over-production of GAB1. It has been shown that inhibiting upstream components of pathways complicit in tumorigenesis can reduce the rate of cancer. This is demonstrated in inhibitions of PI3K in the PI3K pathway. The invention has demonstrated that GAB1 inhibitors exist in a variety of compounds and that they have the potential to reduce the rate of tumorigenesis in humans.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The Grb2-associated binding protein 1 (GAB1) integrates signals from different signalling pathways and is over-expressed in many cancers, therefore representing a new therapeutic target, such as the pleckstrin homology (PH) domain of GAB1 for cancer treatment. Using derived homology models, high-throughput virtual screening of five million compounds resulted in five hits which exhibited strong binding affinities to GAB1 PH domain. Prediction of ligand binding affinities is also in agreement with the experimental $K_D$ values. Furthermore, molecular dynamics studies showed that GAB1 PH domain underwent large conformational changes upon ligand binding. Moreover, these hits inhibited the phosphorylation of GAB1 and demonstrated potent, tumor-specific cytotoxicity against MDA-MB-231 and T47D breast cancer cell lines. This discovery of first-in-class GAB1 PH domain inhibitors may potentially be used for targeted cancer therapy and provides novel insights into structure-based approaches to targeting this protein.

According to one embodiment, the GAB1 PH domain inhibitor comprises a compound of the formula:

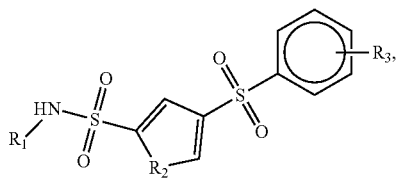

or pharmaceutically acceptable salt thereof. $R_1$ may be of the formula:

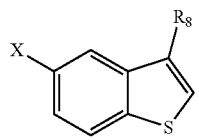

In some embodiments, $R_1$ is an aromatic heterocycle. In some embodiments, $R_8$ is an alkyl. $R_8$ may be attached to the N group of the compound. In other embodiments, X is a halogen. In one embodiment, $R_2$ is an S. In another embodiment, $R_3$ is H, an alkyl, or a halogen.

According to another embodiment, the GAB1 PH domain inhibitor comprises a compound of the formula:

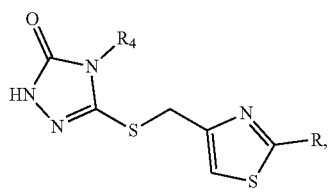

or pharmaceutically acceptable salt thereof. In some embodiments, the compound is an inhibitor of GAB1. In some embodiments, $R_4$ is of the formula:

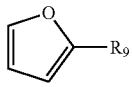

In other embodiments, $R_9$ is an alkyl. In further embodiments, $R_5$ is a benzene, a mono- or poly-substituted aryl group, or other aromatic heterocyle groups.

According to a further embodiment, the GAB1 PH domain inhibitor comprises a compound of the formula:

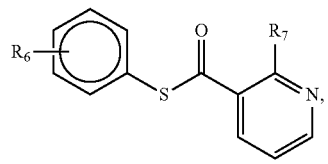

or pharmaceutically acceptable salt thereof. In some embodiments, the compound is an inhibitor of GAB1. In some embodiments, $R_6$ is an H, an akyl, or a halogen. In other embodiments, $R_7$ is of the formula:

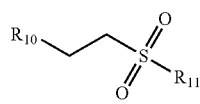

In one embodiment, $R_{10}$ is an S or an alkyl. $R_{10}$ may be bonded to the N-contain aromatic. In another embodiment, $R_{11}$ is an H or an alkyl.

According to one embodiment, a pharmaceutical composition may comprise any of the compounds, and a pharmaceutically acceptable carrier or excipient.

In another embodiment, a method of treating cancer in a mammal in need thereof in described herein. The method may comprise administering to the mammal a therapeutically effective amount of the pharmaceutical composition.

In further embodiments, a method of reducing a tumor size of a tumor, may comprise administering to the tumor a therapeutically effective amount of the pharmaceutical composition.

In still other embodiments, a method of constructing a structure of a protein target, such as GAB1, may comprise obtaining pleckstrin homology (PH) structures, obtaining position-site specific matrixes (PSSM) of the PH structures, identifying secondary structures and homology model templates using the PSSM, modelling homology, and loop refining. In one embodiment, loop refining may further comprise using molecular dynamics (MD) simulations.

BRIEF DESCRIPTION OF THE DRAWINGS

FIG. 2 shows a sequence alignment of the PH domains. IRS1 (PDB ID: 1QQG), TAPP1 (PDB ID: 1EAZ), Myosin X (PDB ID: 3TFM) and DAPP1 (PDB ID: 1FAO). The secondary structure of the generated GAB1 homology model and the crystal structures of the templates are illustrated, using α for α-helix, β for β-sheet. Except for the highly variable $β_{1,2}$ loop regions, the active site residues directly interacting with $PtdIns(3,4,5)P_3$ are highlighted with shadows.

FIG. 7A shows a heavy atom RMSDs for the residues with conformational changes. RMSD of each residue is calculated from the snapshots taken from three independent MD simulations and compared with the unbound control structure. $W107_{GAB1}$ and $W106_{IRS1}$ (in black) are used as the controls for no conformational change. Red: Region I residues; Blue: Region II residues; Magenta: Region III residues. ".." for $p<0.1$; "*" for $p<0.05$; "**" for $p<0.01$. FIGS. 7B-7E shows the critical residues in the three regions in sticks. Pink: the protein in unbound state; Green: the protein in inhibitor-bound state. The inhibitors are depicted with gray sticks and surfaces. The arrows illustrate large conformational changes. FIG. 7B shows GAB1 PH domain in complex with GAB-001; FIG. 7C shows GAB1 PH domain in complex with GAB-017; FIG. 7D shows IRS1 PH domain in complex with GAB-007; and FIG. 7E shows IRS1 PH domain in complex with GAB-010.

FIG. 10A is generated by QMEAN; FIG. 10B is generated by ProSA; and in FIG. 10C, the Ramachandran plot and summary is generated by PROCHECK.

FIG. 17A-17E shows PMFs derived from GAB1-inhibitor complexes;

FIG. 17B shows PMFs derived from GAB1-inhibitor complexes;

FIG. 17C shows PMFs derived from GAB1-inhibitor complexes;

FIG. 17D shows PMFs derived from GAB1-inhibitor complexes;

FIG. 17E shows PMFs derived from GAB1-inhibitor complexes;

FIG. 17F shows PMFs derived from GAB1-inhibitor complexes;

FIG. 17G shows PMFs derived from GAB1-inhibitor complexes;

FIG. 17H shows PMFs derived from IRS1-inhibitor complexes;

FIG. 18A shows show PMFs derived from GAB1-inhibitor complexes;

FIG. 18B shows show PMFs derived from GAB1-inhibitor complexes;

FIG. 18C shows show PMFs derived from GAB1-inhibitor complexes;

FIG. 18D shows show PMFs derived from GAB1-inhibitor complexes;

FIG. 18E shows PMFs derived from GAB1-inhibitor complexes;

FIG. 18F shows PMFs derived from IRS1-inhibitor complexes;

FIG. 18G shows PMFs derived from IRS1-inhibitor complexes;

FIG. 18H shows PMFs derived from IRS1-inhibitor complexes;

DESCRIPTION OF PREFERRED EMBODIMENTS

Figure 1:
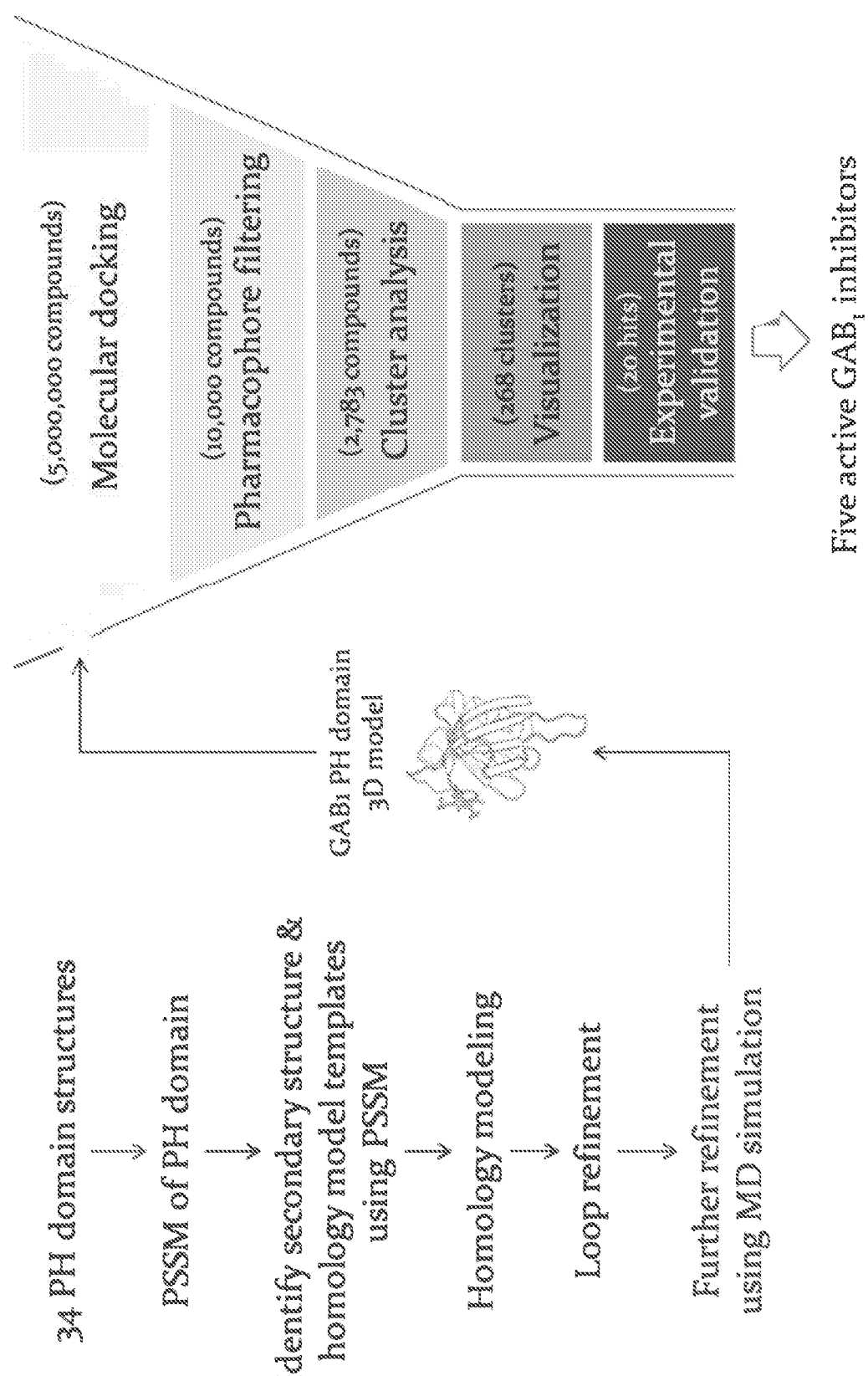
FIG. 1 shows a structure-based drug discovery workflow. All of the available PH domain 3D structures in the PDB were used to build the PSSM scoring functions which were employed to construct the homology model of GAB1 PH domain. The derived structure was used to perform high-throughput virtual screening of five million drug/lead-like compounds. Through a funnel-like process 20 hits were selected for experimental testing and five were confirmed as consistently active in all of the assays.

As used herein, the term "alkyl" as employed herein by itself or as part of another group refers to both straight and branched chain radicals of up to 25 carbons, unless the chain length is otherwise limited, such as methyl, ethyl, propyl, isopropyl, butyl, s-butyl, t-butyl, isobutyl, pentyl, hexyl, isohexyl, heptyl, 4,4-dimethylpentyl, octyl, 2,2,4-trimethylpentyl, nonyl, or decyl.

The term "alkenyl" is used herein to mean a straight or branched chain radical of 2-10 carbon atoms, unless the chain length is otherwise limited, wherein there is at least one double bond between two of the carbon atoms in the chain, including, but not limited to, ethenyl, 1-propenyl, 2-propenyl, 2-methyl-1-propenyl, 1-butenyl, 2-butenyl, and the like. Preferably, the alkenyl chain is 2 to 20 carbon atoms in length, most preferably from 2 to 12 carbon atoms in length.

The term "alkynyl" is used herein to mean a straight or branched chain radical of 2-10 carbon atoms, unless the chain length is otherwise limited, wherein there is at least one triple bond between two of the carbon atoms in the chain, including, but not limited to, ethynyl, 1-propynyl, 2-propynyl, and the like. Preferably, the alkynyl chain is 2 to 20 carbon atoms in length, most preferably from 2 to 12 carbon atoms in length.

In all instances herein where there is an alkenyl or alkynyl moiety as a substituent group, the unsaturated linkage, i.e., the vinyl or ethenyl linkage, is preferably not directly attached to a nitrogen, oxygen or sulfur moiety.

The term "alkoxy" or "alkyloxy" refers to any of the above alkyl groups linked to an oxygen atom. Typical examples are methoxy, ethoxy, isopropyloxy, sec-butyloxy, and t-butyloxy.

The term "aryl" as employed by itself or as part of another group refers to monocyclic or bicyclic aromatic groups containing from 6 to 12 carbons in the ring portion, preferably 6-10 carbons in the ring portion. Typical examples include phenyl, biphenyl, naphthyl or tetrahydronaphthyl.

The term "aralkyl" or "arylalkyl" as employed herein by itself or as part of another group refers to C1-6 alkyl groups as discussed above having an aryl substituent, such as benzyl, phenylethyl or 2-naphthylmethyl.

The term "heterocycle" may refer to a "heteroaryl." "Heteroaryl" as employed herein refers to groups having 5 to 14 ring atoms; 6, 10 or 14 pi electrons shared in a cyclic array; and containing carbon atoms and 1, 2, 3, or 4 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl, phenoxazinyl, and tetrazolyl groups).

The term "heterocycle" may also refer to a "heterocycloalkyl." "Heterocycloalkyls" as used herein may refer to any saturated or partially unsaturated heterocycle. By itself or as part of another group, "heterocycle" may refer to a saturated or partially unsaturated ring system having 5 to 14 ring atoms selected from carbon atoms and 1, 2, 3, or 4 oxygen, nitrogen, or sulfur heteroatoms. Typical saturated examples include pyrrolidinyl, imidazolidinyl, pyrazolidinyl, tetrahydrofuranyl, tetrahydropyranyl, piperidyl, piperazinyl, quinuclidinyl, morpholinyl, and dioxacyclohexyl. Typical partially unsaturated examples include pyrrolinyl, imidazolinyl, pyrazolinyl, dihydropyridinyl, tetrahydropyridinyl, and dihydropyranyl. Either of these systems can be fused to a benzene ring. When a substituent is oxo (i.e., =O), then 2 hydrogens on the atom are replaced. When aromatic moieties are substituted by an oxo group, the aromatic ring is replaced by the corresponding partially unsaturated ring. For example, a pyridyl group substituted by oxo results in a pyridone.

The terms "heteroarylalkyl" or "heteroaralkyl" as employed herein both refer to a heteroaryl group attached to an alkyl group. Typical examples include 2-(3-pyridyl)ethyl, 3-(2-furyl)-n-propyl, 3-(3-thienyl)-n-propyl, and 4-(1-isoquinolinyl)-n-butyl.

The term "cycloalkyl" as employed herein by itself or as part of another group refers to cycloalkyl groups containing 3 to 9 carbon atoms. Typical examples are cyctopropyl, cyclobutyl, cyclopentyl, cyclohexyl, cycloheptyl, cyclooctyl and cyclononyl.

The term "cycloalkylalkyl" or "cycloalkyl(alkyl)" as employed herein, by itself or as part of another group, refers to a cycloalkyl group attached to an alkyl group. Typical examples are 2-cyclopentylethyl, cyclohexylmethyl, cyclopentylmethyl, 3-cyclohexyl-n-propyl, and 5-cyclobutyl-n-pentyl.

The term "cycloalkenyl" as employed herein, by itself or as part of another group, refers to cycloalkenyl groups containing 3 to 9 carbon atoms and 1 to 3 carbon-carbon double bonds. Typical examples include cyclopropenyl, cyclobutenyl, cyclopentenyl, cyclohexenyl, cyclohexadienyl, cycloheptenyl, cycloheptadienyl, cyclooctenyl, cyclooctadienyl, cyclooctatrienyl, cyclononenyl, and cyclononadienyl.

The term "halogen" or "halo" as employed herein by itself or as part of another group refers to chlorine, bromine, fluorine or iodine.

The term "monoalkylamine" or "monoalkylamino" as employed herein by itself or as part of another group refers to the group NH2 wherein one hydrogen has been replaced by an alkyl group, as defined above.

The term "dialkylamine" or "dialkylamino" as employed herein by itself or as part of another group refers to the group NH2 wherein both hydrogens have been replaced by alkyl groups, as defined above.

The term "hydroxyalkyl" as employed herein refers to any of the above alkyl groups wherein one or more hydrogens thereof are substituted by one or more hydroxyl moieties.

The term "haloalkyl" as employed herein refers to any of the above alkyl groups wherein one or more hydrogens thereof are substituted by one or more halo moieties. Typical examples include fluoromethyl, difluoromethyl, trifluoromethyl, trichloroethyl, trifluoroethyl, fluoropropyl, and bromobutyl.

The term "carboxyalkyl" as employed herein refers to any of the above alkyl groups wherein one or more hydrogens thereof are substituted by one or more carboxylic acid moieties.

The term "heteroatom" is used herein to mean an oxygen atom ("O"), a sulfur atom ("S") or a nitrogen atom ("N"). It will be recognized that when the heteroatom is nitrogen, it may form an $NR_aR_b$ moiety, wherein $R_a$ and $R_b$ are, independently from one another, hydrogen or C1 to C8 alkyl, or together with the nitrogen to which they are bound form a saturated or unsaturated 5-, 6-, or 7-membered ring.

The terms "hydroxy" and "hydroxyl" are used interchangeably to refer to the radical —OH. The terms "pyridyl" and "pyridinyl" are used interchangeably to refer to a monovalent radical of pyridine. The terms "carbamoyl" and "aminocarbonyl" are used interchangeably to refer to the radical $NH_2$—C(O)—. The terms "ureido" and "aminocarbonylamino" are used interchangeably to refer to the radical $NH_2$—C(O)—NH—.

"Optional" or "optionally" may be taken to mean that the subsequently described structure, event or circumstance may or may not occur, and that the description includes instances where the event occurs and instances where it does not.

The phrase "optionally substituted" when not explicitly defined refers to a group or groups being optionally substituted with one or more substituents independently selected from the group consisting of hydroxy, nitro, trifluoromethyl, halogen, C1-6 alkyl, C1-6 haloalkyl, C1-6 alkoxy, C1-6 alkylenedioxy, C1-6 aminoalkyl, C1-6 hydroxyalkyl, C2-4 alkenyl, C2-4 alkynyl, C6-10 aryl, phenoxy, benzyloxy, 5-10 membered heteroaryl, C1-6 aminoalkoxy, amino, mono(C1-4)alkylamino, di(C1-4)alkylamino, C2-6 alkylcarbonylamino, C2-6 alkoxycarbonylamino, C2-6 alkoxycarbonyl, C2-6 alkoxycarbonylalkyl, carboxy, C2-6 hydroxyalkoxy, (C1-6)alkoxy(C2-6)alkoxy, mono(C1-4)alkylamino(C2-6)alkoxy, di(C1-4)alkylamino(C2-6)alkoxy C2-10 mono(carboxyalkyl)amino, bis(C2-10 carboxyalkyl)amino, C2-6 carboxyalkoxy, C2-6 carboxyalkyl, carboxyalkylamino, guanidinoalkyl, hydroxyguanidinoalkyl, cyano, trifluoromethoxy, perfluoroethoxy, amino carbonylamino, mono(C1-4)alkylaminocarbonylamino, di(C1-4)alkylaminocarbonylamino, N—(C1-4)alkyl-N-aminocarbonylamino, N—(C1-4)alkyl-N-mono(C1-4)alkyl aminocarbonyl-amino or N—(C1-4)alkyl-N-di(C1-4)alkylaminocarbonylamino.

"Administering" when used in conjunction with a therapeutic means to administer a therapeutic directly into or onto a target tissue or to administer a therapeutic to a patient whereby the therapeutic positively impacts the tissue to which it is targeted. Generally speaking, the term "tissue" refers to any aggregation of similarly specialized cells, which are united in the performance of a particular function. "Administering" a composition may be accomplished by oral administration, injection, infusion, absorption or by any method in combination with other known techniques. Such combination techniques include heating, radiation and ultrasound.

The term "target", as used herein, refers to the material for which either deactivation, rupture, disruption or destruction or preservation, maintenance, restoration or improvement of function or state is desired. For example, diseased cells, pathogens, or infectious material may be considered undesirable material in a diseased subject and may be a target for therapy.

The term "improves" is used to convey that the present invention changes the appearance, form, characteristics and/or physical attributes of the tissue to which it is being provided, applied or administered. "Improves" may also refer to the overall physical state of an individual to whom an active agent has been administered. For example, the overall physical state of an individual may "improve" if one or more symptoms of a cancer are alleviated by administration of an active agent.

As used herein, the term "therapeutic" means an agent utilized to treat, combat, ameliorate or prevent an unwanted condition or disease of a patient. The terms "therapeutically effective amount" or "therapeutic dose" as used herein are interchangeable and may refer to the amount of an active agent or pharmaceutical compound or composition that elicits a biological or medicinal response in a tissue, system, animal, individual or human that is being sought by a researcher, veterinarian, medical doctor or other clinician. A biological or medicinal response may include, for example, one or more of the following: (1) preventing a disease, condition or disorder in an individual that may be predisposed to the disease, condition or disorder but does not yet experience or display pathology or symptoms of the disease, condition or disorder, (2) inhibiting a disease, condition or disorder in an individual that is experiencing or displaying the pathology or symptoms of the disease, condition or disorder or arresting further development of the pathology and/or symptoms of the disease, condition or disorder, and (3) ameliorating a disease, condition or disorder in an individual that is experiencing or exhibiting the pathology or symptoms of the disease, condition or disorder or reversing the pathology and/or symptoms experienced or exhibited by the individual.

The term "treating" may be taken to mean prophylaxis of a specific disorder, disease or condition, alleviation of the symptoms associated with a specific disorder, disease or condition and/or prevention of the symptoms associated with a specific disorder, disease or condition. In some embodiments, the term refers to slowing the progression of the disorder, disease or condition or alleviating the symptoms associated with the specific disorder, disease or condition. In some embodiments, the term refers to slowing the progression of the disorder, disease or condition. In some embodiments, the term refers to alleviating the symptoms associated with the specific disorder, disease or condition. In some embodiments, the term refers to restoring function, which was impaired or lost due to a specific disorder, disease or condition.

The term "patient" generally refers to any living organism to which compounds described herein are administered and may include, but is not limited to, any non-human mammal, primate or human. Such "patients" may or may not be exhibiting the signs, symptoms or pathology of the particular diseased state.

The term "pharmaceutical composition" shall mean a composition including at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan. A pharmaceutical composition may, for example, contain an GAB1 inhibitor or a pharmaceutically acceptable salt of the GAB1 inhibitor as the active ingredient.

For the purposes of this disclosure, a "salt" is any acid addition salt, preferably a pharmaceutically acceptable acid addition salt, including but not limited to, halogenic acid salts such as hydrobromic, hydrochloric, hydrofluoric and hydroiodic acid salt; an inorganic acid salt such as, for example, nitric, perchloric, sulfuric and phosphoric acid salt; an organic acid salt such as, for example, sulfonic acid salts (methanesulfonic, trifluoromethan sulfonic, ethanesulfonic, benzenesulfonic or p-toluenesulfonic), acetic, malic, fumaric, succinic, citric, benzoic, gluconic, lactic, mandelic, mucic, pamoic, pantothenic, oxalic and maleic acid salts; and an amino acid salt such as aspartic or glutamic acid salt. The acid addition salt may be a mono- or di-acid addition salt, such as a di-hydrohalogenic, di-sulfuric, di-phosphoric or di-organic acid salt. In all cases, the acid addition salt is used as an achiral reagent which is not selected on the basis of any expected or known preference for interaction with or precipitation of a specific optical isomer of the products of this disclosure.

"Pharmaceutically acceptable salt" is meant to indicate those salts which are, within the scope of sound medical judgment, suitable for use in contact with the tissues of a patient without undue toxicity, irritation, allergic response and the like, and are commensurate with a reasonable benefit/risk ratio. Pharmaceutically acceptable salts are well known in the art.

As used herein, the term "daily dose amount" refers to the amount of pramipexole per day that is administered or prescribed to a patient. This amount can be administered in multiple unit doses or in a single unit dose, in a single time during the day or at multiple times during the day. A "dose amount" as used herein, is generally equal to the dosage of the active ingredient, which may be administered per day. For example, a non-effective dose amount of 1 mg/day to 10,000 mg/day of a GAB1 inhibitor. The term "unit dose" as used herein may be taken to indicate a discrete amount of the therapeutic composition that contains a predetermined amount of the active compound. The amount of the active compound is generally equal to the dosage of the active ingredient, which may be administered on or more times per day. For example, the unit dose may be a fraction of the desired daily dose which may be given in fractional increments, such as, for example, one-half or one-third the dosage.

Referring now to FIG. 1-19, the present invention features a compound of the formula:

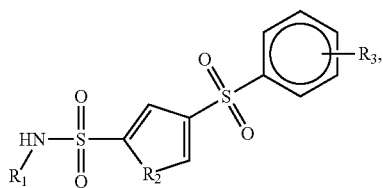

or a pharmaceutically acceptable salt thereof. In some embodiments, the compound is an inhibitor of GAB1.

In some embodiments, $R_1$ is of the formula:

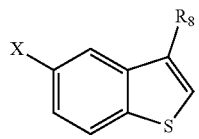

In some embodiments, $R_1$ is an aromatic heterocycle. In some embodiments, $R_8$ is an alkyl. In some embodiments, $R_8$ is attached to the N group of the compound. In some embodiments, X is a halogen, such as chlorine. In some embodiments, $R_2$ is an S. In some embodiments, $R_3$ is H, an alkyl, or a halogen, such as chlorine.

In another embodiment, the present invention features a compound of the formula:

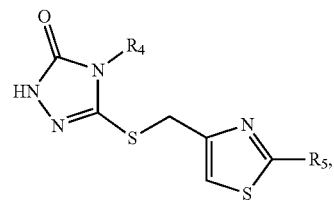

or a pharmaceutically acceptable salt thereof. In some embodiments, the compound is an inhibitor of GAB1.

In some embodiments, $R_4$ is of the formula:

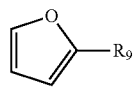

In some embodiments, $R_9$ is an alkyl. In some embodiments, $R_5$ is a benzene, a mono- or poly-substituted aryl group, or other aromatic heterocyle groups.

In further embodiments, the present invention features a compound of the formula:

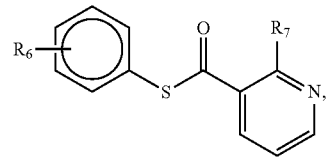

or a pharmaceutically acceptable salt thereof. In some embodiments, the compound is an inhibitor of GAB1.

In some embodiments, $R_6$ is an H, an alkyl, or a halogen such as chlorine. In other embodiments, $R_6$ may be 1, 2, or 3 substituents. For example, $R_6$ may indicate a double substitution with halogens. In some embodiments, $R_7$ is of the formula:

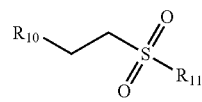

In some embodiments, $R_{10}$ is an S or an alkyl. $R_{10}$ may be bonded to the N-contain aromatic. In some embodiments, $R_{11}$ is an H or an alkyl.

In some embodiments, $R_1$ through $R_{11}$, independently, may be —H, —CH$_3$, —CH$_2$CH$_3$, —CH$_2$(CH$_2$)$_m$CH$_3$, —C(CH$_3$)$_3$, —CH$_2$CH$_2$R$_{12}$, —OH, —OCH$_3$, CH$_2$OH, —C(O)OH, —CH$_2$C(O)OH, —CH$_2$CH$_2$C(O)OH, —C(O)R$_{12}$, —C(O)OR$_{12}$, —CH$_2$C(O)OR$_{12}$, —CH$_2$CH$_2$C(O)OR$_{12}$, —NH$_2$, CH$_2$NH$_2$, —NHC(O)CH$_3$, —S(O)$_2$R$_{12}$, —CH$_2$S(O)$_2$R$_{12}$, C$_6$H$_5$, —C$_6$H$_4$R$_4$, —CH$_2$C$_6$H$_5$, —S(O)$_2$C$_6$H$_5$, —CH$_2$S(O)$_2$C$_6$H$_5$, C$_1$-C$_{20}$ alkyl heteroaryl, heteroarylalkyl, morpholino, or halogen. In some embodiments, $R_{12}$ is —H, —OH, —NH$_2$, —CH$_3$, —CH$_2$CH$_3$, —CH$_2$CH$_2$CH$_3$, —OCH$_3$, —C(O)OH, —C$_6$H$_5$, —C$_6$H$_4$R$_{13}$, —CH$_2$C$_6$H$_5$, —CH$_2$C$_6$H$_4$R$_{13}$, halogen, heteroaryl, heteroarylalkyl, or piperazinyl. In some embodiments, $R_{13}$ is —H, —OH, —NH$_2$, —CH$_3$, —CH$_2$CH$_3$, —CH$_2$CH$_2$CH$_3$, —C(O)OH, or halogen. In some embodiments, the C$_1$-C$_{20}$ alkyl is optionally substituted with one or more substituents independently selected from halogen, OH, —NH$_2$, —NHC(O)R$_{14}$, and —NR$_{14a}$R$_{14b}$. In some embodiments, $R_{14}$ is aryl, heteroaryl, or C$_1$-C$_{20}$ alkyl. In some embodiments, each of the aryl, heteroaryl, or C$_1$-C$_{20}$ alkyl are each optionally substituted with one or more substituents independently selected from —NH$_2$, —OH, —CH$_3$, —CH$_2$CH$_3$, —CH$_2$CH$_2$CH$_3$, C$_{1-6}$ alkyl, —C$_6$H$_5$, —C$_6$H$_4$R$_{15}$, —CH$_2$C$_6$H$_5$, —CH$_2$C$_6$H$_4$R$_{15}$, and halogen. In some embodiments, $R_{14a}$ may be H or methyl. In some embodiments, $R_{14b}$ may be methyl, 7-nitrobenzo[c][1,2,5]oxadiazol-4-yl, or —C(O)C$_6$H$_5$. In some embodiments, $R_{15}$ is —H, —CH$_3$, heteroaryl, —C(CH$_3$)$_3$, —OH, —NH$_2$, NHC(O)CH$_3$, S(O)$_2$OH, —P(O)$_2$OH, As(O)$_2$OH, NO$_2$, —OCH$_3$, —OCH$_2$CH$_3$, —C(O)OH, —C(O)NH$_2$, or halogen.

In some embodiments, the present invention features compounds that inhibit GAB1. In some embodiments, the compounds are selected from the following compounds:

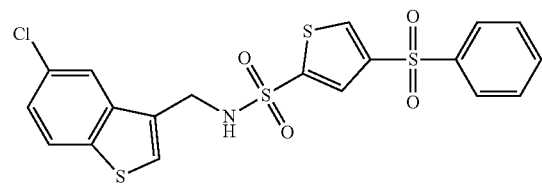

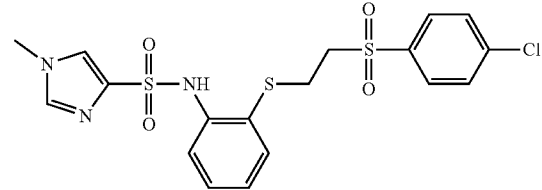

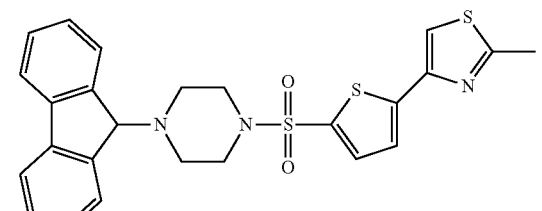

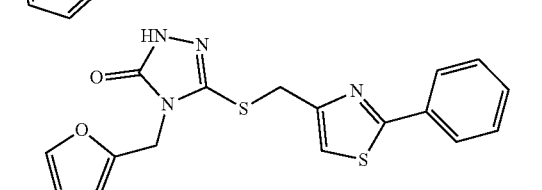

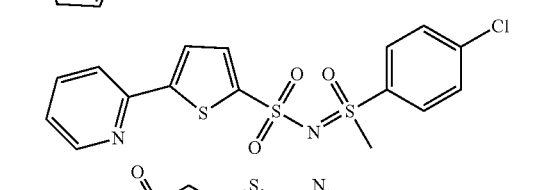

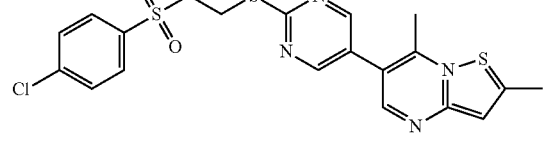

-continued

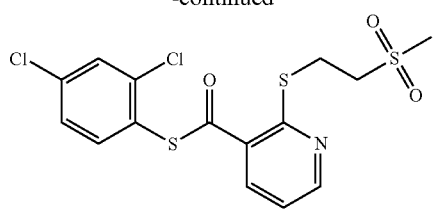

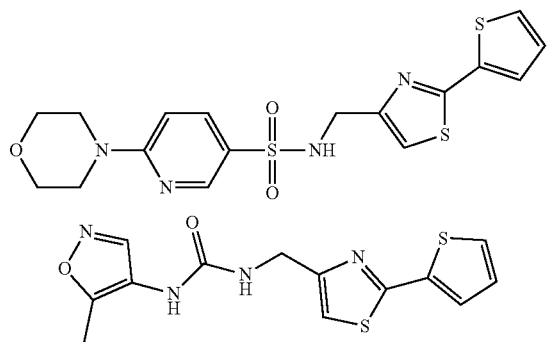

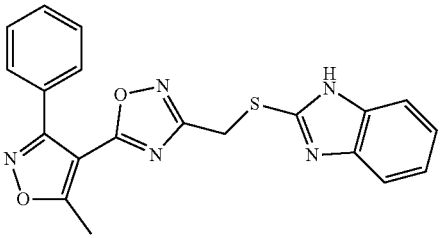

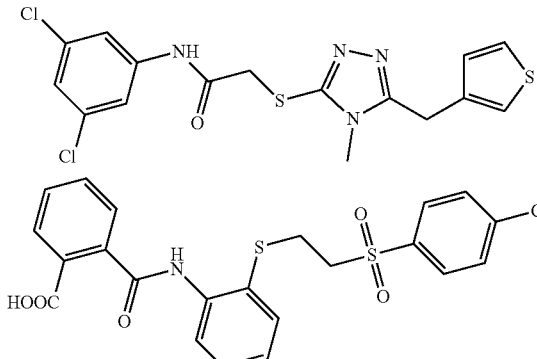

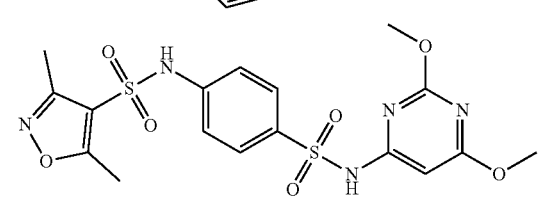

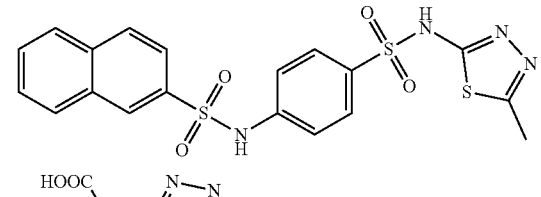

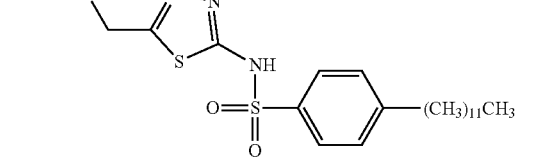

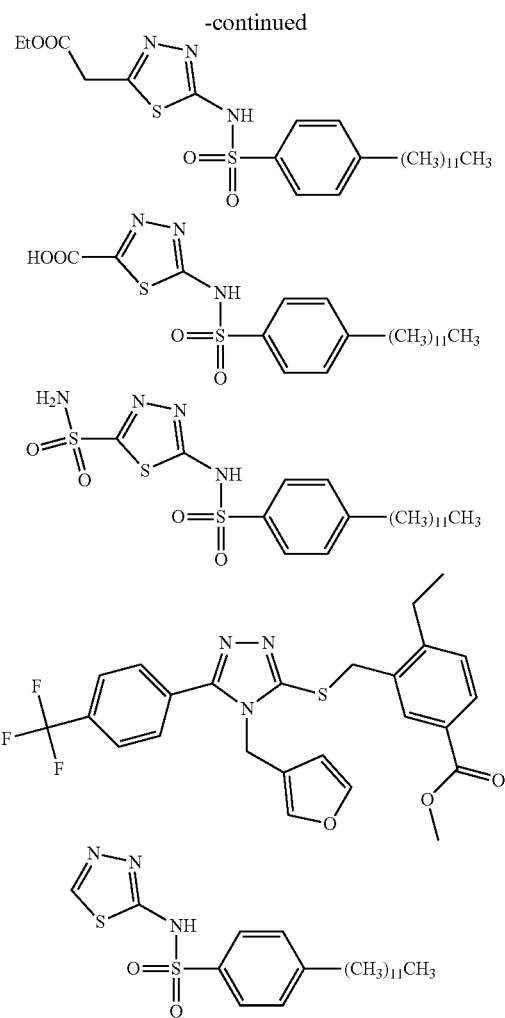

In some embodiments, the present invention features a pharmaceutical composition comprising a compound according to any of the previously mentioned compounds, or pharmaceutically acceptable salts thereof, and a pharmaceutically acceptable carrier or excipient.

In preferred embodiments, the compounds in the pharmaceutical composition may inhibit GAB1. In some embodiments, the present invention also features a method of treating cancer in a mammal in need thereof, said method comprising administering to the mammal a therapeutically effective amount of the pharmaceutical composition.

In some embodiments, the cancer is breast cancer. In some embodiments, the breast cancer is triple negative breast cancer. In some embodiments, the cancer is prostate cancer. In some embodiments, the cancer is lung cancer. In some embodiments, the mammal is a human. In some embodiments, the pharmaceutical composition is administered orally, topically, or injected at or near a cancerous tissue. In some embodiments, the pharmaceutical composition is administered at a dose of about 0.01 mg/kg to about 1,000 mg/kg, about 1000 mg/kg to about 5,000 mg/kg, or about 5000 mg/kg to about 10,000 mg/kg. In other embodiments, the dose is administered about daily, 2-4 times per day, weekly, or 2-4 times per week.

In other embodiments, the present invention features a method of reducing a tumor size of a tumor. According to one embodiment, the method may comprise administering to the tumor a therapeutically effective amount of the pharmaceutical composition. In one embodiment, the pharmaceutical composition is administered orally, topically, or injected at or near the tumor. In another embodiment, the pharmaceutical composition is administered at a dose of about 0.01 mg/kg to about 1,000 mg/kg, about 1000 mg/kg to about 5,000 mg/kg, or about 5000 mg/kg to about 10,000 mg/kg. In other embodiments, the dose is administered about daily, 2-4 times per day, weekly, or 2-4 times per week.

In still other embodiments, the present invention further features a method of constructing a structure of a protein target. According to one embodiment, the method may comprise obtaining pleckstrin homology (PH) structures, obtaining position-site specific matrixes (PSSM) of the PH structures, identifying secondary structures and homology model templates using the PSSM, modelling homology, and loop refining. In one embodiment, loop refining may further comprise using molecular dynamics (MD) simulations. In some embodiments, the protein target is GAB1.

The following illustrate non-limiting examples of the present invention.

Chemical Dataset

A collection of five million drug and lead-like compounds which were curated from various sources (e.g., PubChem and MayBridge) was used for virtual screening. LigPrep was employed for ligand preparation, including the removal of salts, assignment of appropriate protonation, tautomerization and ring conformations, and generation of 3D structures by energy minimization with OPLS2001 force field. Additionally, an internal collection of 167 previously synthesized inhibitors targeting AKT PH domain were included for virtual screening.

PSSM and Sequence Logo Representation

Figure 8:
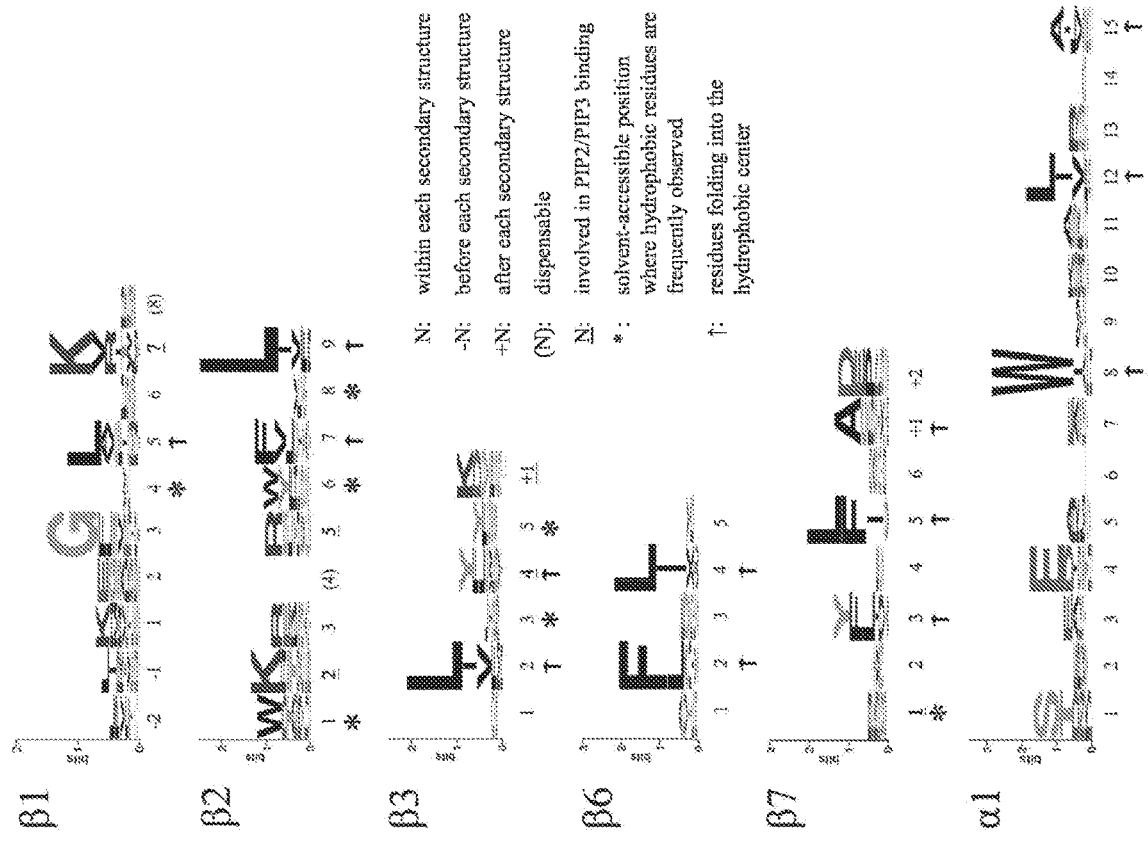
FIG. 8 shows sequence logos for PH domain, specifically, the position-specific logos for the secondary structure elements of PH domain (generated by Weblogo server). $β_4$ and $β_5$ are not included because of the high variation within these two β-sheets. The size of residue indicates the relative frequency of the residue at the corresponding position.

A total of 65 high-resolution crystal structures of PH domains were obtained from PDB, and 34 non-redundant proteins were curated. Their PDB IDs are listed in Table 4. They were used for secondary structure-based sequence alignment with STRAP. The multiple sequence alignments for $\beta_1$, $\beta_2$, $\beta_3$, $\beta_6$, $\beta_7$ and $\alpha_1$ secondary structural fragments were extracted. The individual alignment will be used as input to PSI-BLAST which could generate a PSSM for each individual fragment as shown in Table 5. These PSSMs can be represented by WebLogo for more intuitive visualization and understanding (FIG. 8). These FIGures were generated using the WebLogo server.

3D Structure Prediction of GAB1 PH Domain in Complex with IP4

The sequence of GAB1 PH domain was retrieved from UniProt database (accession number Q13480). The secondary structure was predicted by PSSM combined with PSIPRED and aligned to the templates (myosin X (PDB ID: 3TFM), IRS1 (PDB ID: 1QQG), TAPP1 (PDB ID: 1EAZ) and DAPP1 (PDB ID: 1FAO) for homology modeling. To improve the quality of homology modeling, the multiple sequence alignment generated by ClustalX were manually corrected to ensure each secondary structure elements (e.g., α-helix and (β-sheets) were properly aligned. GAB1 PH domain homology models were built using MODELLER 9v10. As the active site residues of DAPP1 have the highest homology to those of GAB1 PH domain, the coordinates of the IP4 co-crystallized with DAPP1 was used as the initial structure. The initial 1,000 homology models were generated. Since the lysine-rich loop $\beta_{1,2}$ is important for phosphoinositide binding, especially for Group 1 PH domain, the $\beta_{1,2}$ loop of top ten initial models (evaluated by DOPE score) were subjected to ligand-steered refinement using built-in function of MODELLER. Five models were selected out of the 100 generated loop models based on the overall DOPE scores, Ramachandran plot, and the consistencies to IP4 binding site features and the reported mutagenesis studies. These five GAB1-IP4 complex models were refined by MD simulations using AMBER10 available at Texas Advanced Computing Center. All MD simulations were performed in triplicates with different initial velocities. The MD simulations were performed using ff99SB force field in TIP3P explicit solvent with particle mesh Ewald (PME), periodic boundary conditions and SHAKE. The topology and charges of the ligand were generated by Antechamber with AM1-BCC charges. The system is solvated and neutralized in the cuboid box in which the closest distance between any atom originally in solute and the edge of the box is 12 Å. The system was equilibrated for 100 ps, and the production MD simulations were run in NPT ensemble for 20 ns, with the time step=2 fs. The snapshots were taken every 1 ps. The root mean square deviation (RMSD) relative to the first frame and the root mean square fluctuation (RMSF) relative to the average structure were analyzed with cpptraj implemented in AmberTools12. The average structures were minimized, and the model quality was evaluated by QMEAN, ProSA and PROCHECK. A reasonable protein model should have both ProSA and QMEAN Z-scores within the range for the native proteins of similar size, as illustrated by FIG. 8.

Virtual Screening

GOLD 5.1 was employed for virtual screening on a high performance computing cluster using the GAB1-IP4 complex model derived above. Molecular docking was performed with flexible side chains of the residues involved in IP4 binding, and the conformation with the best score of each compound was ranked based on their ChemPLP scores. Protein pharmacophore modeling was performed using GRID v22c. Briefly, the GRID calculations were performed with a grid box enclosing the target with 1 Å beyond each dimension. During the calculations, the GRID directive Move was set (MOVE=1) to allow the flexibility of the side chains. The molecular interaction fields (MIFs) were computed to determine the interaction between the receptor atoms and three different probes: the hydrophobic (DRY), the amide nitrogen (N1, H bond donor), and the carbonyl oxygen (O, H bond acceptor). Via visual inspection of the local minima of the GRID energy maps, the favorable binding sites of these three probes were used to define the features of a pharmacophore query. The derived pharmacophores were used to evaluate the binding poses of the initially selected 10,000 hits out of the five million compounds. If the docked hit poses fit the pharmacophore, they would be selected and subjected to clustering analysis based on the MACCS fingerprints and Tanimoto coefficient. The best scored compound from each cluster was chosen and the binding poses of these hits were individually inspected based on molecular visualization.

3D Structure Refinement of GAB1/IRS1 PH Domain in Complex with Inhibitors

In order to evaluate the selectivity of the inhibitors, the PH domain (IRS1 or GAB1)-inhibitor complex structures were optimized using MD simulations. The starting conformation for MD simulation is the binding mode which obtained the best score in molecular docking. The MD simulations were performed in triplicates for 50 ns using the parameters described in "3D structure prediction of GAB1 PH domain in complex with IP4" section. The trajectories of GAB1-GAB-001 complex, GAB1-GAB-017, and IRS1-GAB-010 were also generated. Each trajectory contained 1,000 snapshots which were taken every 50 ps. The ligands and the critical residues were in sticks, whereas the backbones of PH domain proteins were in ribbons. Starting from the docking conformation, these MD trajectories vividly demonstrated the conformational changes of the PH domain proteins upon ligand binding.

PMF-Based Binding Free Energy Calculation

Briefly, for the routine of PMF-based computation of protein-ligand absolute binding free energy, the average structure of protein-ligand complex obtained from three independent 50 ns MD simulations was subject to energy minimization to remove clashes. The resulted structure was considered as the reference frame to define the position and orientation constraints. The PMF as a function of mass-weighted RMSD ($\xi$) relative to the reference ligand or the protein-ligand distance (r) was sampled by umbrella sampling and weighted-histogram analysis method (WHAM).

Figure 16:
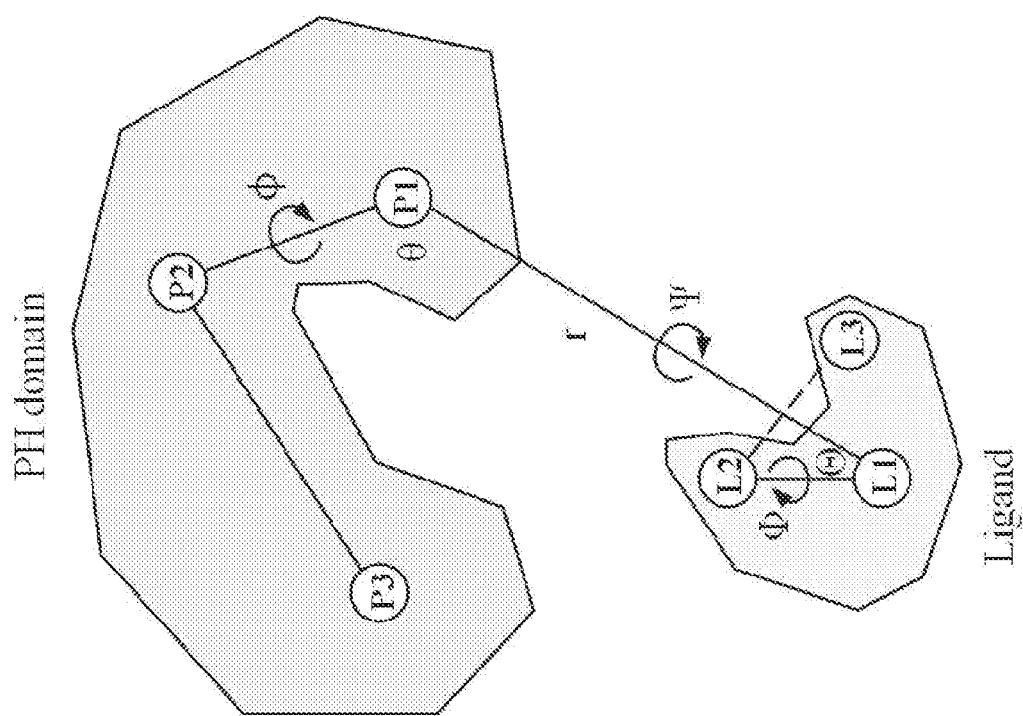
FIG. 16 shows a schematic representation of frame of reference used to define the position and orientation restraints. To reduce the degrees of freedom, P1, P2, P3 and L1, L2, L3 were employed to represent the coordinates of the protein and the ligand, respectively.
Figure 17:
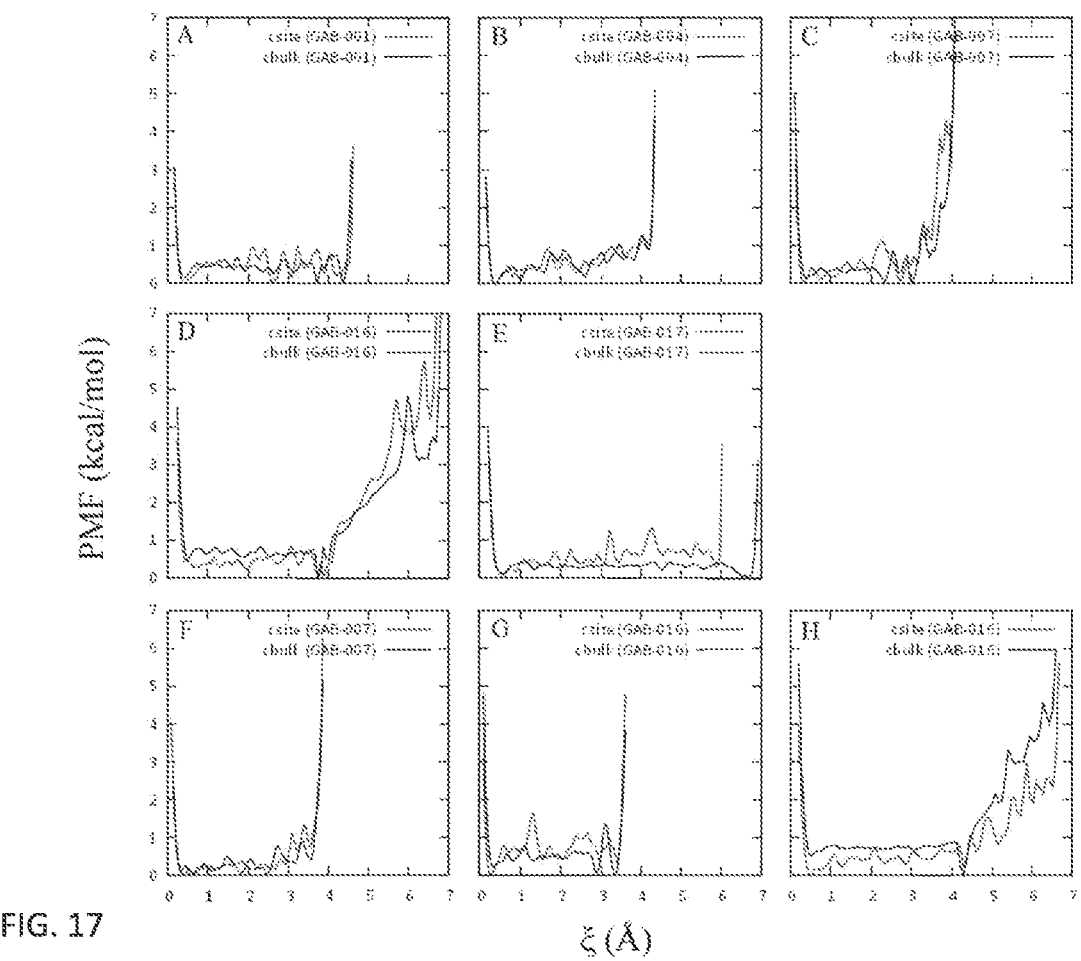
FIG. 17 shows a ligand conformational PMF as a function of mass-weighted RMSD (ξ). The ligand in the bulk is in black lines, whereas the ligand in the active site is in read lines. More specifically.
Figure 18:
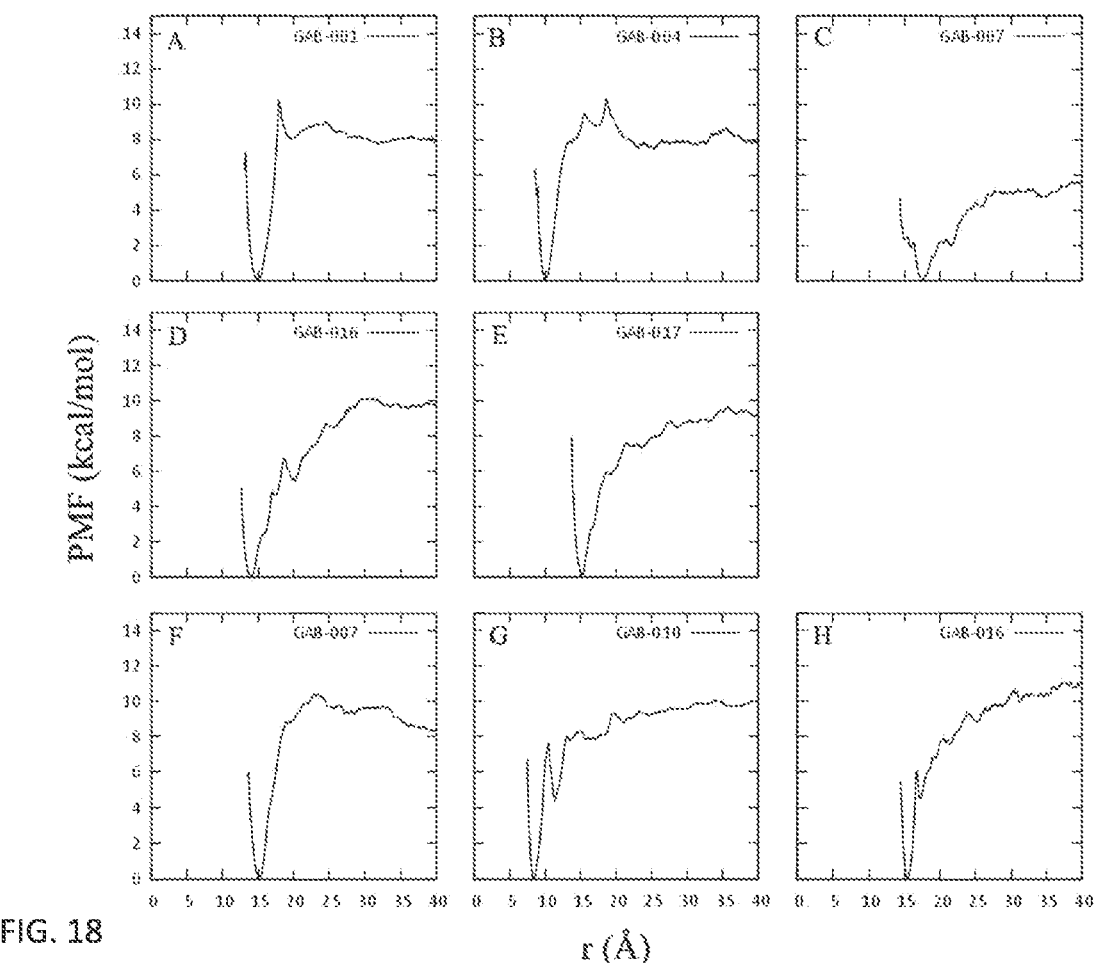
FIG. 18 shows separation PMF as a function of L1-P1 distance (r). More specifically.

The explicit derivation of this PMF method is a statistical mechanics methodology which calculates the binding free energy by introducing hypothetical intermediate states representing the association pathway of ligand from the unbound "bulk" regions to the ligand-binding "site". The average structure obtained from above 50 ns MD simulations was subject to energy minimization to remove structural defects. The resulted protein-ligand complex structure was employed as the reference frame to define the position and orientation restraints, as illustrated in FIG. 16. The position of the ligand with respect to its receptor protein is defined in a spherical coordinate system (r, θ, φ), whereas the orientation of the ligand is defined by a series of Euler angles (Θ, Φ, Ψ). r is the L1-P1 distance; φ is the L1-P1-P2 angle; ϕ is the L1-P1-P2-P3 dihedral angle; Θ is the P1-L1-L2 angle; Φ is the P1-L1-L2-L3 dihedral angle; φ is the P2-P1-L1-L2 dihedral angle. The harmonic potentials were applied to restrain the orientational and axial degrees of freedom with u(Θφϕ) and $u_a$(θ, φ), where $$u_o(\Theta, \Phi, \Psi) = \frac{1}{2}k_0[(\Theta - \Theta_{ref})^2 + (\Phi - \Phi_{ref})^2 + (\Psi - \Psi_{ref})^2], \text{ and}$$

$$u_a(\theta, \phi) = \frac{1}{2}k_a[(\theta - \theta_{ref})^2 + (\phi - \phi_{ref})^2], \text{ respectively.}$$

The choice of atoms to define L1, L2, L3, P1, P2, P3 can be arbitrary, as validated before. However, an attempt to standardize the definition of these points is as follows: L1 is the ligand center of mass; L2 and L3 are two terminal moieties relative to L1; P1 is the center of mass of the conserved L45, F85 and W107 (GAB1) or L44, S95 and W106 (IRS1); P2 is the center of mass of the proline residues in β1,2 loop; P3 is the center of mass of β6,7 loop.

The term, corresponding to the conformational restraints on the ligand free in solution, was calculated by Eq. 1, in which $w_c^{bulk}(\xi)$ is the PMF as a function of (the mass-weighted RMSD with respect of the reference ligand conformation). $w_c^{bulk}(\xi)$ was simulated by umbrella sampling in the presence of a conformational restraint with harmonic potential $u_c = \frac{1}{2}k_c(\xi[\text{ligand}; \text{ligand}_{ref}])^2$ and without the orientational and axial restraints, using the force constant $k_c=2$ kcal/mol Å$^2$. The umbrella sampling simulation for $w_c^{bulk}(\xi)$ were separated by 0.2 Å, and for each window, 1 ns production simulation was performed followed by 0.2 ns equilibration. For the ligands with dodecyl moiety (GAB-016 and GAB-017), the maximum RMSD was 8 Å, corresponding to a total of 40 umbrella sampling windows. Otherwise, the maximum RMSD was 6 Å (totally 30 windows). The PMF in the bulk was calculated with the weighted histogram analysis method (WHAM).

Similarly, as' (the conformational restraints on the ligand in the binding site) was calculated by Eq. 2. The corresponding PMF $w_c^{bulk}(\xi)$ was computed with the same parameters and methodology employed when computing $w_c^{bulk}(\xi)$, except that the umbrella sampling simulations were done in the presence of protein.

$$e^{-\beta G_c^{bulk}} = \frac{\int d\xi e^{-\beta[w_c^{bulk}(\xi)+u_c(\xi)]}}{\int d\xi e^{-\beta[w_c^{bulk}(\xi)]}}, \quad (1)$$

$$e^{-\beta G_o^{site}} = \frac{\int d\xi e^{-\beta[w_c^{site}(\xi)+u_c(\xi)]}}{\int d\xi e^{-\beta[w_c^{site}(\xi)]}}, \quad (2)$$

For umbrella sampling simulations along the axis r, the window configurations were generated with a biasing radial potential $u(r)=\frac{1}{2}k_r(r-r')^2$ in which the force constant $kr=2$ kcal/mol Å². The windows were spaced by 0.5 Å, and the maximum L1-P1 distance (r*) was 40 Å. Of note, the r* is an arbitrary value, but it does not affect the final binding free energy value. The umbrella sampling simulations were done in the presence of the positional and orientational restraints. To accommodate the possible conformational changes during ligand separation, very soft harmonic potentials were applied on orientational and axial restraints, with ka=ko=0.2 kcal/mol rad². The inventors performed 0.5 ns production simulation followed by 0.2 ns equilibration for each window. The resulted PMF along r axis, w(r), was used to calculate the separation PMF (I*) by integration of the Boltzmann constant (Eq. 5).

Other terms, such as S* and $G_o^{bulk}$, were calculated from Eq. 3 and Eq. 4 by direct numerical integrations. The contribution of free energy costs of orientational restriction ($G_a^{size}$) and axial restriction ($G_a^{size}$) in the binding site were ignored, as a very soft force constant (0.2 kcal/mol-rad2) was used. Still, the sum of ($G_o^{size}$) and $G_a^{size}$ as estimated at an order of 0.01 kcal/mol using Eq. 6, assuming the PMF for any angular or torsional restraints is similar with that for the original work. X in Eq. 6 represents any angular degree of freedom, including $\theta$, $\varphi$, $\Theta$, $\phi$, $\psi$.

$$S^* = (r^*)^2 \int_0^\pi \sin(\theta)d\theta \int_0^{2\pi} d\phi e^{-\beta u_a(\theta,\phi)}, \quad (3)$$

$$e^{-\beta G_o^{bulk}} = \frac{1}{8\pi^2}\int_0^\pi \sin(\Theta)d\Theta \int_0^{2\pi} d\Phi \int_0^{2\pi} d\Psi e^{-\beta u_o(\Theta,\Phi,\Psi)}, \quad (4)$$

$$I^* = \int_{site} dr e^{-\beta[w(r)-w(r^*)]}, \quad (5)$$

$$e^{-\beta G_X^{site}} = \quad (6)$$

$$\frac{\int dXe^{-\beta[w_X^{site}(X)+\frac{1}{2}k_0(X-X_{ref})^2]}}{\int dXe^{-\beta w_X^{site}(X)}} = 0.9992 \Rightarrow G_X^{site} \approx 0.0005 \text{ kcal/mol},$$

The final binding free energy $\Delta G_{bind}$ was calculated using Eq. 7, where $C^0$ is the standard state concentration of 1 mol/L (=1/1,661 Å³)

$$\Delta G_{bind} = -\frac{1}{\beta}\ln(S*I*C^\circ) + G_c^{bulk} + G_o^{bulk} \overbrace{-G_o^{site} - G_a^{site}}^{<0.01 \text{ kcal/mol}} - G_c^{site} \quad (7)$$

$$\approx -\frac{1}{\beta}\ln(S*I*C^\circ) + G_c^{bulk} + G_o^{bulk} - G_c^{site}$$

The experimental binding free energies were derived from experimental $K_D$ (or $K_i$) using the equation $\Delta G_{bind}=RT \ln(K_D)$ or $\Delta G_{bind}=RT \ln(K_i)$.

Surface Plasmon Resonance (SPR) Spectroscopy Binding Assays

The DNA sequences of human GAB1 and IRS1 PH domain (IRS1 is for selectivity evaluation) were cloned into pGEX-4T1 inducible bacterial expression plasmid (GeneStorm, Invitrogen, Carlsbad, Calif.) transformed into BL21 (DE3) E. Coli. Expression and purification of the recombinant proteins were performed. Binding assays were performed using a Biacore 2000 instrument with the Biacore Control Software v3.2 and BIAevaluation v4.1 analysis software (Biacore, Piscataway, N.J.). Briefly, the PH domain GST-fusion proteins were immobilized on a CM5 Sensorchip (Biacore BR-1000-12) using Biacore's Amine Coupling Kit (Biacore BR-1000-50) to a level of 10,000 Response units (RUs). Small molecule analytes at concentrations ranging from one tenth to ten times the predicted $K_D$ were injected at a high flow rate (30 µL/min). Dimethylsulfoxide (DMSO) concentrations in all samples and running buffer were 1% (v/v) or less. For the competitive binding assays and $K_i$ determination, PtdIns(3,4,5)P$_3$-biotin labeled liposomes (Echelon Biosciences, Salt Lake City, Utah) and SA chips were used with increasing concentrations of the compound tested. The inventors did triplicate SPR assays for each concentration.

Cellular Proliferation Assay

Two human breast cancer Cell lines and one normal breast cell line were used for this study: T47D ductal missing highlighted section in original pg. 26Type Culture Collection, Rockville, Md.). T47D and MDA-MB-231 cells were maintained in bulk culture in Dulbecco's modified Eagle medium (DMEM) supplemented with 10% heat-inactivated fetal bovine serum (FBS), 4.5 g/L glucose, 100 U/mL penicillin and 100 mg/mL streptomycin in a 5% CO$_2$ atmosphere. MCF-10A cells were maintained in MEGM with other conditions same as the cancer cell lines. Cells were passaged using 0.25% trypsin and 0.02% EDTA. Cells were confirmed to be mycoplasma free by testing them with an ELISA kit (Roche-Boehringer Mannheim, Indianapolis, Ind.). The hit compounds were freshly prepared in DMSO at a stock concentration of 10 mM. For the evaluation of cellular proliferation, a standard 96-well micro-cytotoxicity assay was performed as described in reference. Briefly, the assay was set up by plating cells at 5,000-10,000 cells per well (depending on cell doubling time) for a growth period of 4 days. The identified hits were added directly to the media, dissolved in DMSO at various concentrations ranging from 1 to 200 µM. The endpoint was spectrophotometric determination of the reduction of 3-(4,5-dimethylthiazol-2-yl)-2,5-diphenyltetrazolium bromide. All assays were performed in triplicates.

Inhibition of GAB1 and IRS1 Phosphorylation

For all biological assays, hit compounds were added at 20 µM concentration directly into the culture media of the cells for 4 hr following a 16 hr incubation of T47D cells without FBS. Cells were stimulated with HGF for 20 min at 50 ng/ml. Following this treatment, cells were lysed and equal amounts of total cell lysate were loaded on a pSer[312]-IRS-1/Total IRS-1 Meso Scale Discovery plate as described by the manufacturer. The plate was read using a Sector™Imager 2400A instrument (Meso Scale Discovery protein profiling system, Gaithersburg, Md.). For the measurement of GAB1 phosphorylation, T47D cells were treated as for the phosphorylation of IRS1 evaluation. Cell lysates were run on a 7% SDS-PAGE and membrane were probed with specific anti-phospho-Tyr$^{627}$ GAB1 (Cell signaling). Each experiment was performed at least three times.

Fold Recognition and Sequence Alignment

PH domains are unique due to their conserved secondary structures and 3D folds, all with seven β-sheets and a C-terminal helix. However, the pairwise sequence identities among different PH domains are usually below 30%, and the loop regions are hypervariable in length and amino acid sequence. Herein, the inventors collected all available 34 non-redundant crystal structures of PH domains from Protein Data Bank (PDB) and performed secondary structure-based sequence alignment using STRAP. From the sequence alignment, the inventors generated PSSMs for $β_1$, $β_2$, $β_3$, $β_6$, $β_7$ and $α_1$ (presented as sequence logos in FIG. 8) to guide secondary structure prediction of new PH domain (e.g., GAB1). As no reliable PSSMs for $β_4$ and $β_5$ were generated due to low sequence similarity, the inventors used PSIPRED server to predict these two β-sheets.

FIG. 8 shows the sequence logos derived from the collected 34 PH domains, in which the size of residue indicates the relative frequency of that residue at the corresponding position. As expected, the most conserved residues are found in the hydrophobic cores of PH domains. The residues responsible for phosphoinositide binding are generally located at $β_1[7]$, $β_2[2]$, $β_2[5]$, $β_3[4]$, $β_3[+1]$ and $β_7[1]$ (the number in the brackets indicates the residue position at the secondary structure element). Predominantly, they are basic residues such as lysine and arginine. These observations were combined with PSSM and PSIPRED to predict the secondary structure of GAB1 PH domain, and found the predicted structure preserves a typical β-sandwich fold where C8-K14, W26-L33, V44-Y48, R58-D61, Q66-G71, I84-N88, and R92-V97 form the respective seven β-sheets, while E101-I114 forms the C-terminal α-helix (FIG. 2). However, the GAB1 PH domain is unique with: 1) a long $β_{1,2}$ loop landmarked by the conserved K14 and W26, similar to myosin X (PDB ID: 3TFM); 2) a long $β_{2,3}$ loop, similar to IRS1 (PDB ID: 1QQG); 3) a long $β_{5,6}$ loop, similar to TAPP1 (PDB ID: 1EAZ); 4) the highest sequence identity of active-site residues (except for $β_{1,2}$ loop region) to DAPP1 (PDB ID: 1FAO) (shadowed residues in FIG. 2). Therefore, the above four proteins were chosen as the templates for the following-up homology modeling studies.

Homology Modeling and Structural Optimization with Molecular Dynamics

Figure 9:
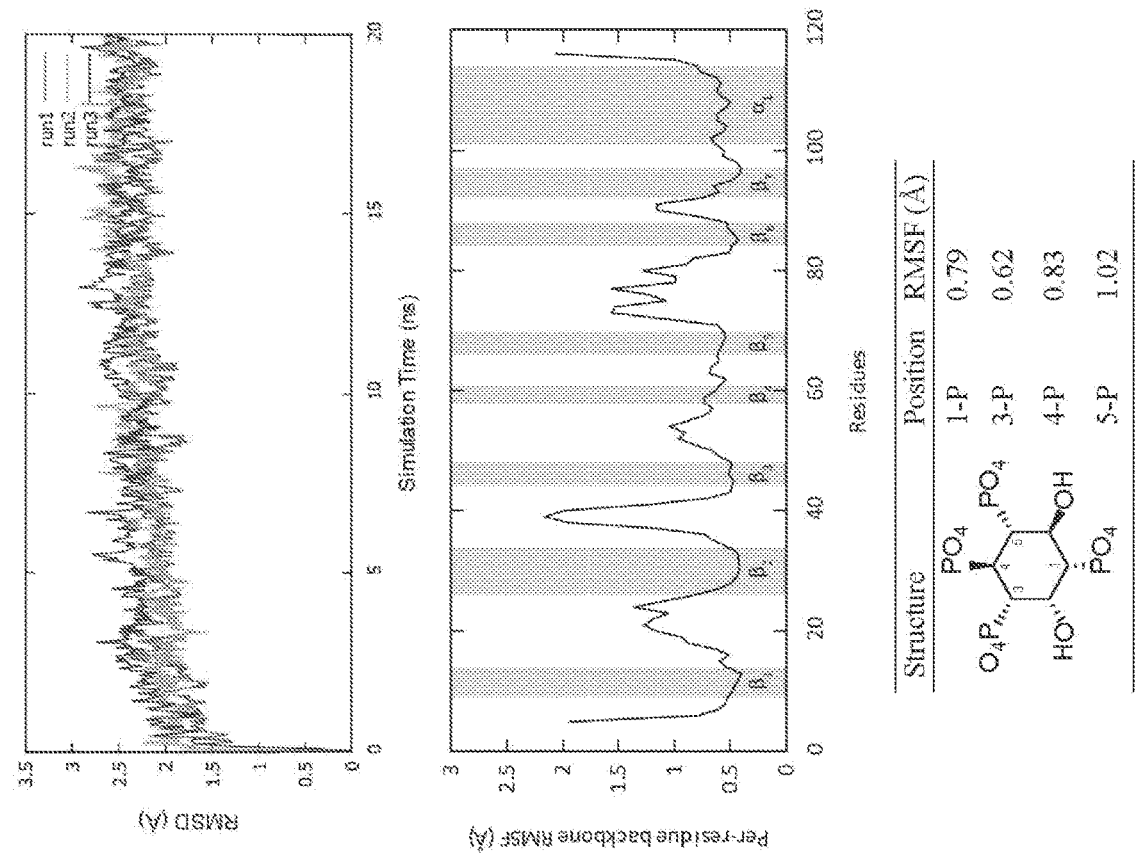
FIG. 9 shows a backbone RMSD and per-residue backbone RMSF for GAB1-IP4 complex. The simulation lasted for 20 ns. The mass-weighted average RMSFs were calculated for each residue based on backbone atoms. Atomic RMSFs of four phosphates in IP4 were shown in the last table.
Figure 10A:
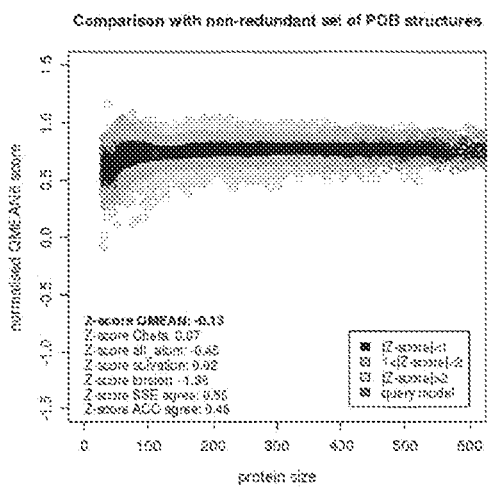
FIGS. 10A-10C show a quality of GAB1 PH domain model, where the model was subjected to energy minimization prior to quality assessment.
Figure 10B:
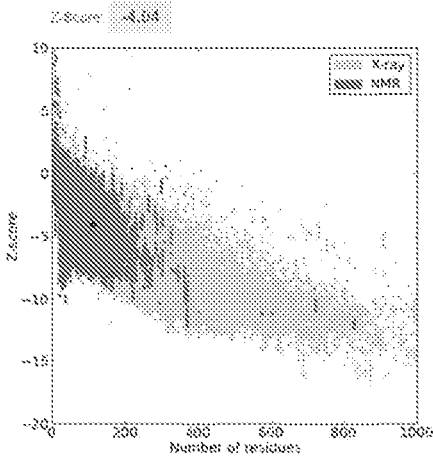
Figure 10C:
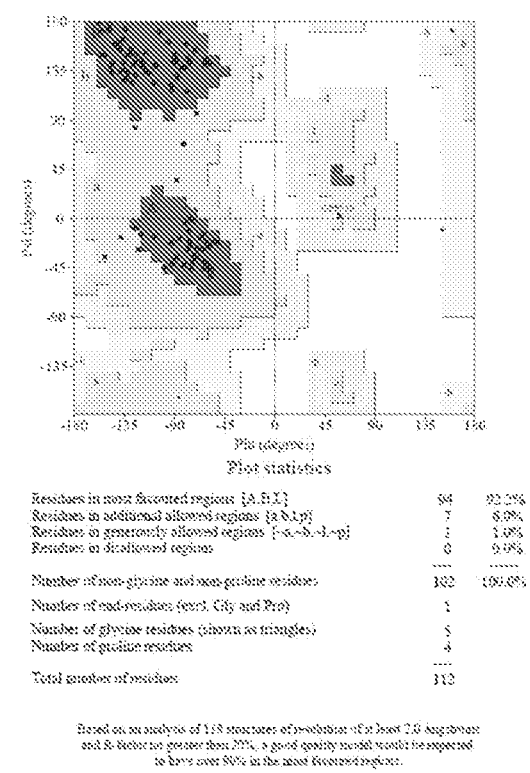
Figure 11:
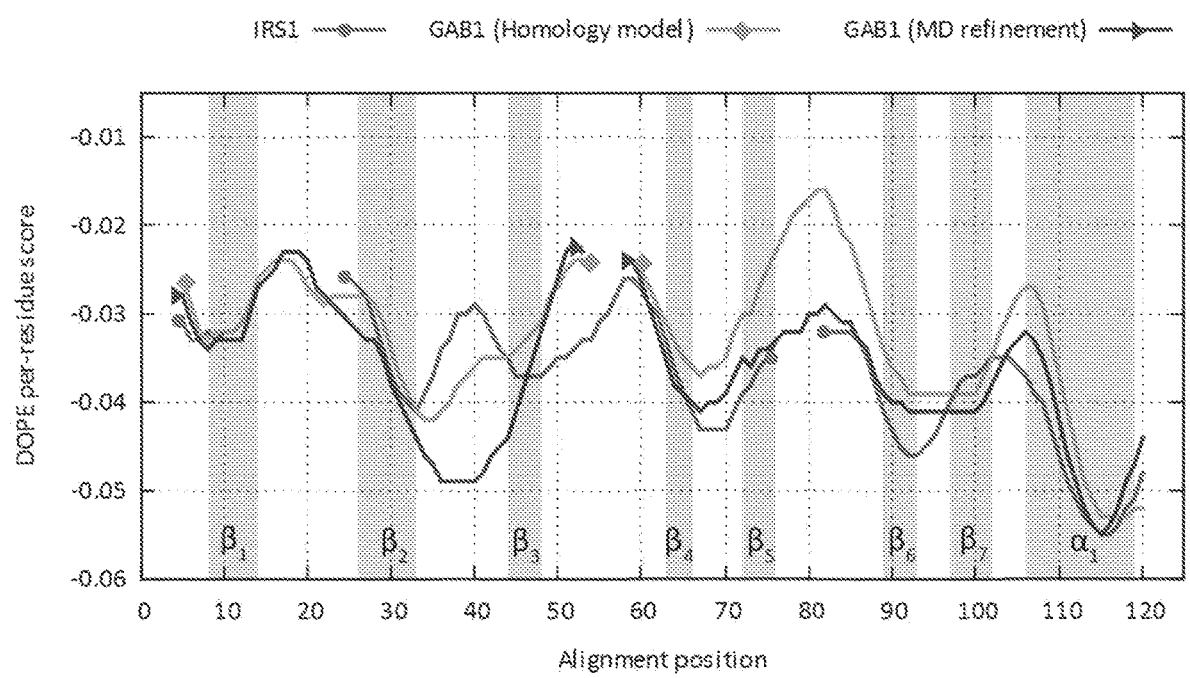
FIG. 11 shows a comparison of DOPE score profiles. IRS1 (PDB ID: 1QQG), GAB1 homology model and the lowest energy GAB1 model with MD simulation refinement were compared. The MD refinement model was subject to 1000 steps energy minimization with ff99SB force field to remove transient structural defects. The secondary structure is annotated at the bottom.

The inventors constructed 1,000 homology models of GAB1 PH domain in complex with inositol-tetrakisphosphate (IP4) based on the X-ray crystal structures of four aforementioned templates. After loop refinement and molecular dynamics (MD) simulation, one reliable model was selected in which IP4 binds stably to GAB1 PH domain with a minor fluctuation of phosphates (RMSF<1.1 Å), shown in FIG. 9. The simulation of this model reached the equilibrium after 5 ns, as judged by the RMSD of all of the backbone atoms (C, CA and N) (FIG. 9). Large fluctuations of the Cα atoms were only observed in the $β_{1,2}$, $β_{2,3}$ and $β_{5,6}$ loops (FIG. 9). The quality of the lowest-energy model was assessed by QMEAN, ProSA and PROCHECK. The Ramachandran plot showed reasonable backbone dihedral angles: 92.2% of the residues were in the most favored regions, and eight residues in the additional or generously allowed regions. Both the ProSA Z-score (−4.04) and QMEAN Z-score (−0.13) of final model were within the range as typically seen for the native proteins of the similar size (FIGS. 10A-10C). In addition, the DOPE per-residue profile demonstrated a significant decrease in the DOPE scores at the $β_{2,3}$ loop, $β_{4,5}$ loop, $β_5$, $β_{5,6}$ loop and $β_6$ for the refined structure compared with the initial homology model (FIG. 11).

Figure 3A:
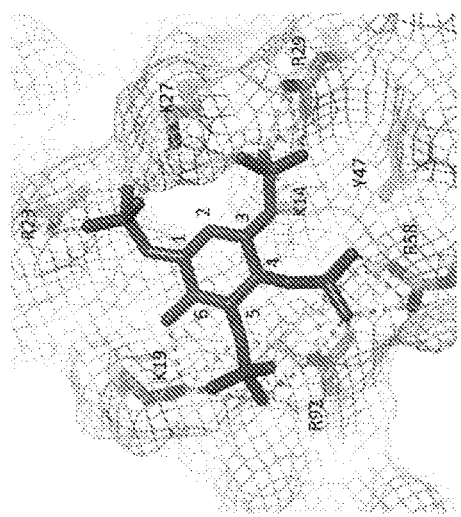
FIG. 3A shows a 3D model of GAB1 PH domain with an overall structure of IP4-bound GAB1 PH domain. The protein secondary structure is shown in ribbons and IP4 is shown in sticks.
Figure 3B:
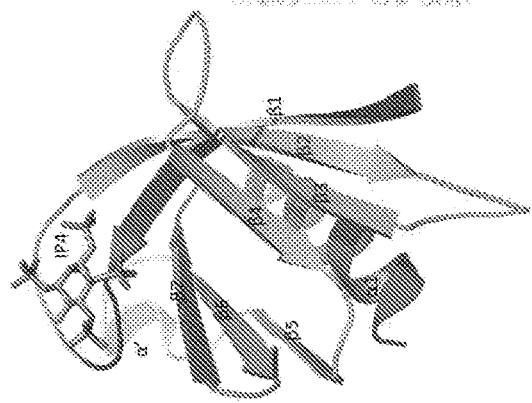
FIG. 3B shows a 3D model of GAB1 PH domain with a close view of the IP4 binding site. The critical residues for IP4 binding are labeled, and IP4 is in black stick with position labeled. The hydrogen bonds are illustrated with dashes.
Figure 3C:
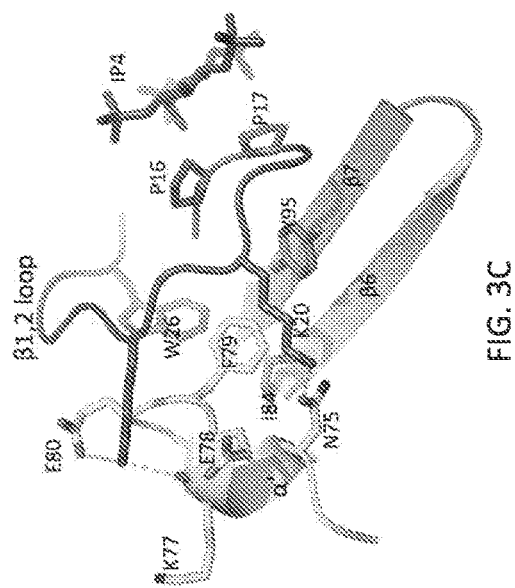
FIG. 3C shows interactions between α'-helix and $β_{5,6}$ loop. The residues mediating the interactions are highlighted with sticks and hydrogen bonds are illustrated with dashes.
Figure 4:
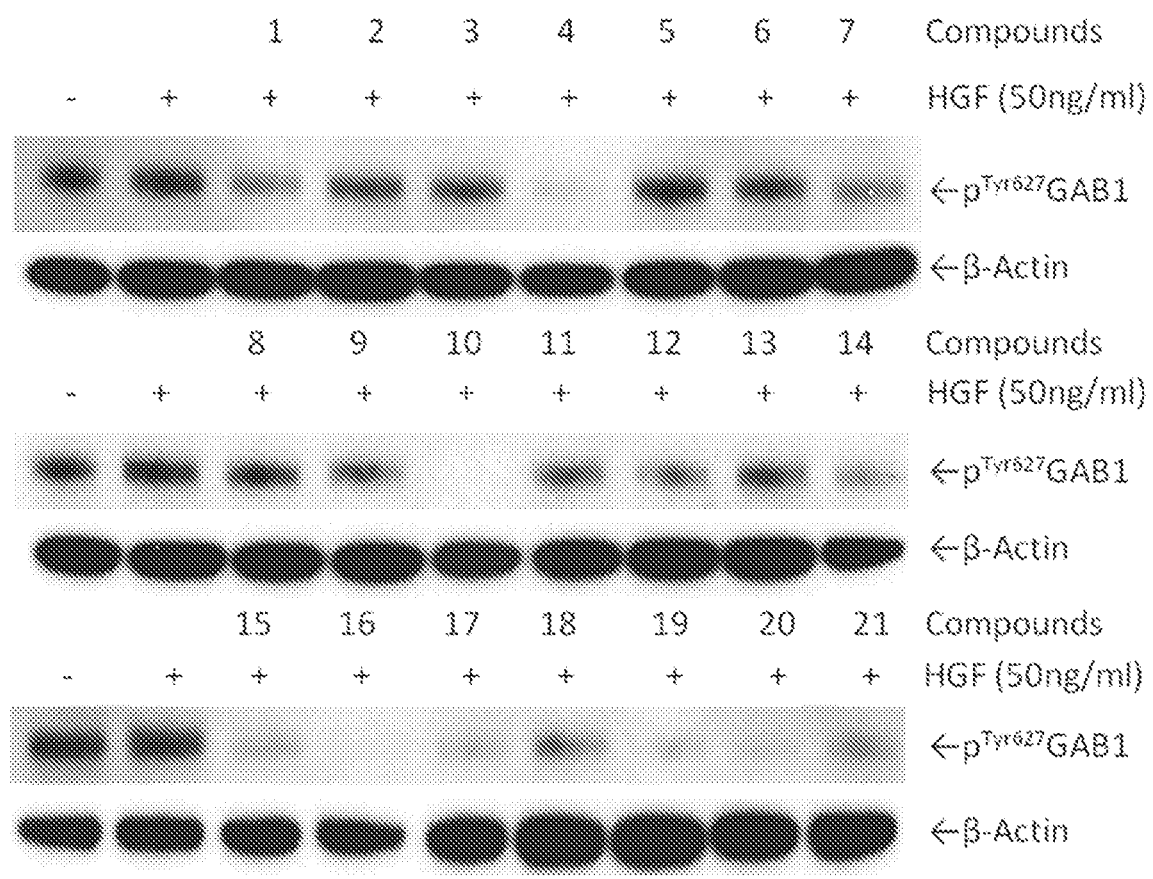
FIG. 4 shows an inhibition of Y627 phosphorylation in GAB1. No. 1-20 are GAB-001 to GAB-020, and No. 21 is DPIEL.

As illustrated by FIG. 3A, the 3D model of GAB1 PH domain maintained the conserved β-sandwich folding. Similar to other Group 1 PH domains (e.g., Grp1 and Btk), the phosphoinositide-binding site of GAB1 was surrounded by the $β_{1,2}$, $β_{3,4}$ and $β_{6,7}$ loops. The 2-hydroxyl group of IP4 oriented towards the $β_{1,2}$ loop, and the 3,4,5-phosphates intensively interacted with the aforementioned basic residues in the $β_1$, $β_2$, $β_4$ and $β_7$. Particularly, K19 and R23 in the $β_{1,2}$ loop formed hydrogen bonds with 5-P and 1-P, respectively (FIG. 3B). This explains why GAB1 PH domain specifically binds to PtdIns(3,4,5)P$_3$ but not PtdIns (3,4)P$_2$ or PtdIns(4,5)P$_2$. Strikingly, the sequence motif NKKEFE in the $β_{5,6}$ loop folded into an additional α-helix, as termed α. This additional α-helix also occurs in phospholipase Cδ PH domain (PDB ID: 1MAI), and it interacts with W26, F79 and Y95 in the $β_{1,2}$ loop via hydrogen bonding networks and hydrophobic interactions (FIG. 3C). This α-helix was likely to stabilize the IP4-bound conformation of $β_{1,2}$ loop, as W26A or W26C mutation impairs the PtdIns(3,4,5)P$_3$ binding. Furthermore, the motif SPP in the $β_{1,2}$ loop formed intensive vdW interactions with the $β_7$ and inositol scaffold (FIG. 3C). Finally, GAB1 PH domain had an extra hydrophobic region (later defined as Region II) due to the smaller side chains of those hydrophobic residues around $β_{6,7}$ loop compared to IRS1. All these specific structural features intrinsically offered possibility of designing selective inhibitors against GAB1 over other PH domains, as further discussed in the ligand-induced conformational changes section.

In Silico Hit Identification

Figure 12:
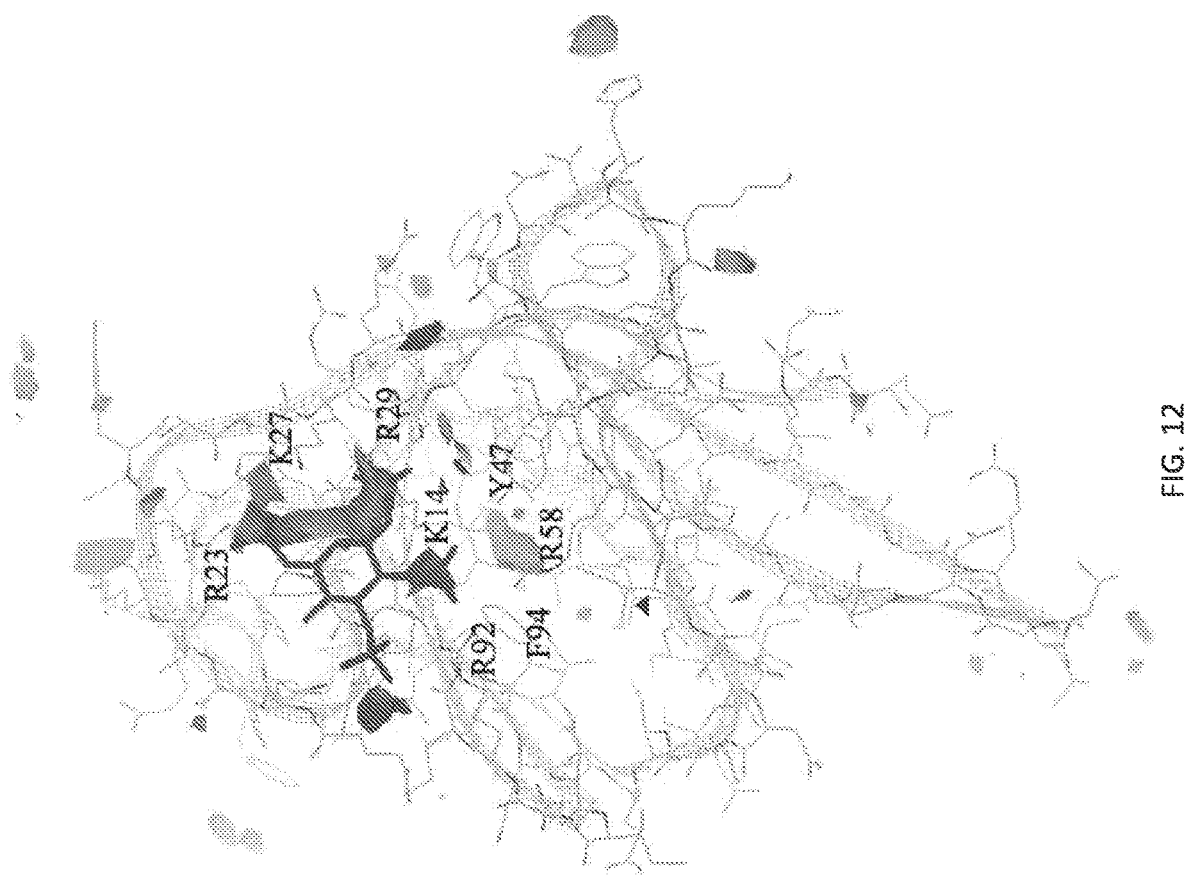
FIG. 12 shows isovolume of GAB1 PH domain generated by GRID. The area favoring H-bond acceptor (−6.0 kcal/mol) was displayed in magenta surface, whereas area favoring hydrophobic (−2.0 kcal/mol) probes was displayed in green surface. The protein backbone is illustrated with cyan lines, and the ligand (IP4) is in blue sticks. The crucial residues are labeled around isovolume surface.
Figure 13:
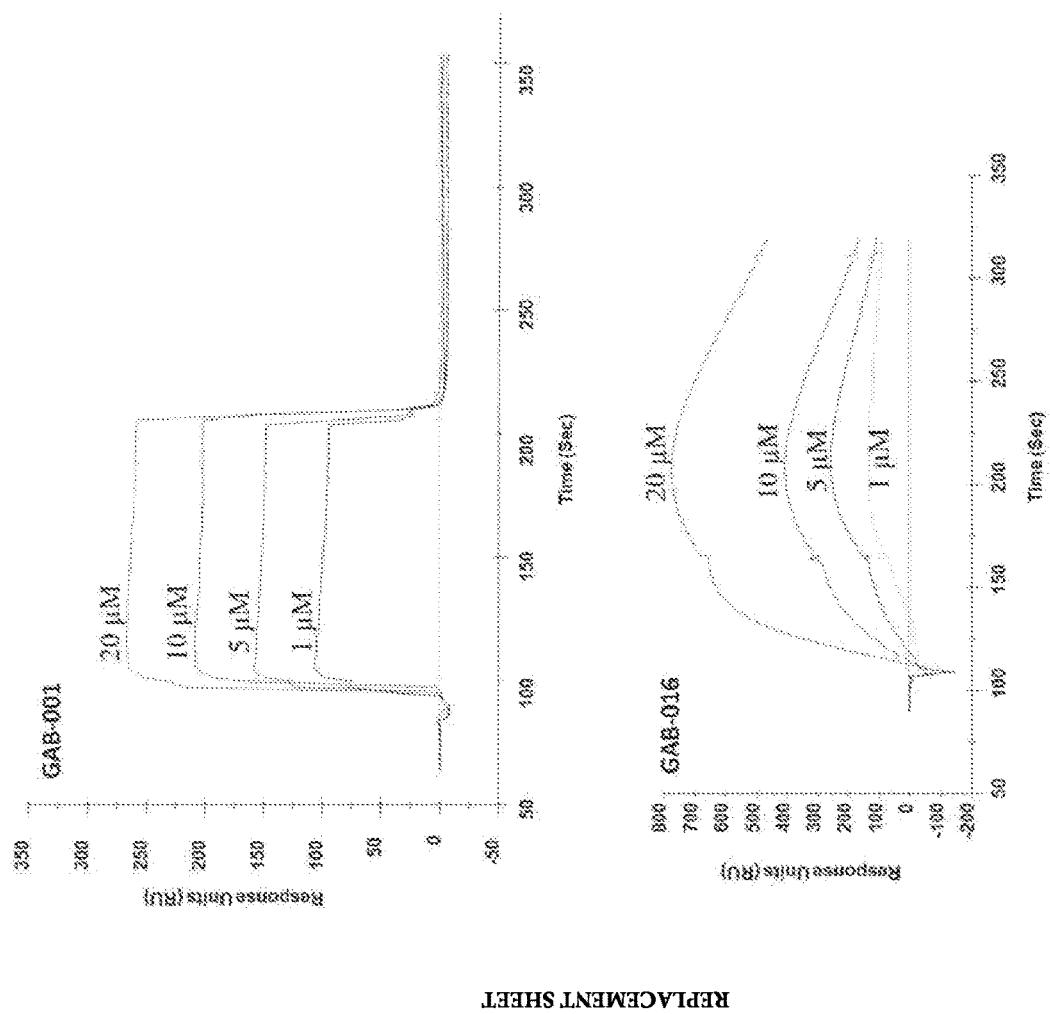
FIG. 13 shows SPR of GAB-001, GAB-016 binding to GAB1 PH domain.

To identify novel inhibitors of GAB1 PH domain, the inventors performed structure-based virtual screening using the D-refined structural model. Additionally, a protein-based pharmacophore filter was derived using GRID method to select those high-throughput virtual screening hits of which the docked poses matched the pharmacophores. Residues K14, R23, K27, R29, R58 and R92 were identified as the residues that favorably interact with hydrogen bond acceptors, whereas Y47, F94 and I60 were specified as the preferential areas for hydrophobic moieties (FIG. 12). The residues responsible for PtdIns(3,4,5)P$_3$ binding were predicted to be K14, K27, R29, Y47, K49, R58 and R92, consistent to the mutagenesis studies. These critical residues were employed to define the protein pharmacophores to select docking poses of those 10,000 top ranked hits (only based on docking scores ranging 43.47-101.39) from the virtual screening of over five million compounds of the in-house collection. The resulted 2,783 hits were subjected to cluster analysis based on their chemical diversity (Tanimoto coefficient<0.65), and the inventors obtained 268 clusters and selected the best-scored hits from each cluster (FIG. 1). Upon visualizing their molecular interactions with the GAB1 PH domain, 20 hits were chosen, as listed in Table 1.

TABLE 1
Biochemical and biological activities of hits.
| Structure | ID | $K_n$ or $K_i$ (μM) | | | % pGAB1 inhibition | IC$_{50}$ (μM) | |
| --- | --- | --- | --- | --- | --- | --- | --- |
| | | GAB1 | IRS1 | AKT1 | | MDA-MB-231 | T47D |
| 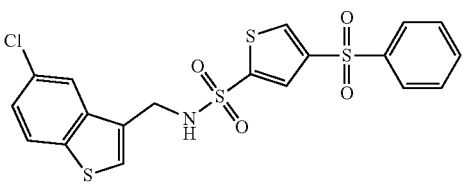 [SMILES: O=S(=O)(NCc1csc2ccc(Cl)cc12)c1cc(S(=O)(=O)c2ccccc2)cs1] | GAB-001 | 9.38 ± 1.60* | ND | ND | 55 | 40.3 ± 1.3 | 23.7 ± 2.7 |
| 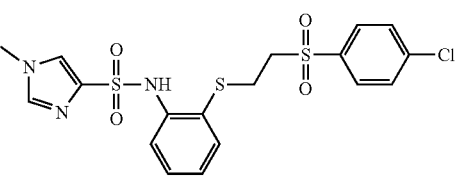 [SMILES: Cn1cnc(S(=O)(=O)Nc2ccccc2SCCS(=O)(=O)c2ccc(Cl)cc2)c1] | GAB-002 | 2.1 ± 0.1 | 16.4 ± 4.3 | ND | 32 | 142.7 ± 11.6 | 137.6 ± 6.9 |
| 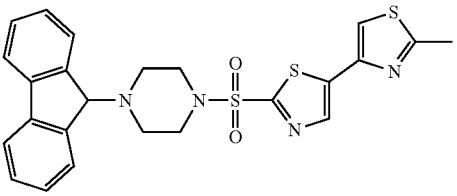 [SMILES: Cc1nc(-c2cnc(S(=O)(=O)N3CCN(C4c5ccccc5-c5ccccc54)CC3)s2)cs1] | GAB-003 | 2.7 ± 0.8 | 3.3 ± 1.5 | ND | 14 | 85.2 ± 7.2 | 13.9 ± 0.6 |
| 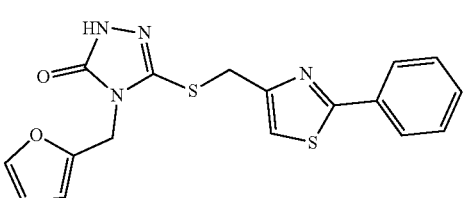 | GAB-004 | 2.2 ± 1.1 | NB | ND | 81 | 66.6 ± 4.6 | 19.4 ± 2.9 |
| 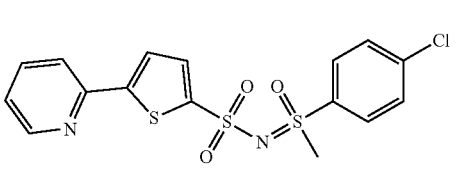 [SMILES: CS(=O)(=NS(=O)(=O)c1ccc(-c2ccccn2)s1)c1ccc(Cl)cc1] | GAB-005 | NB | NB | ND | 6 | IA | IA |
| 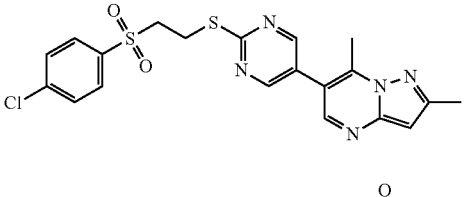 | GAB-006 | NB | NB | ND | 16 | ND | 100.8 ± 1.8 |
| 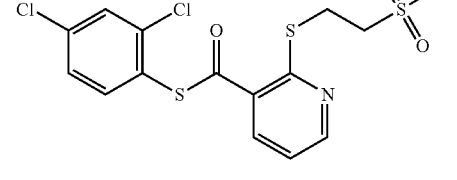 | GAB-007 | 42.3 ± 8.9 | 1.6 ± 0.2 | ND | 53 | 4.6 ± 0.7 | 20.1 ± 4.3 |

TABLE 1-continued

Biochemical and biological activities of hits.

| Structure | ID | $K_d$ or $K_i$ (μM) | | | % pGAB1 inhibition | IC$_{50}$ (μM) | |
|---|---|---|---|---|---|---|---|
| | | GAB1 | IRS1 | AKT1 | | MDA-MB-231 | T47D |
| 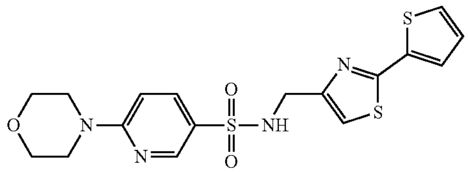 [SMILES: O=S(=O)(NCc1csc(-c2cccs2)n1)c1ccc(N2CCOCC2)nc1] | GAB-008 | NB | 16.2 ± 1.7 | ND | 8 | IA | 43.2 ± 3.2 |
| 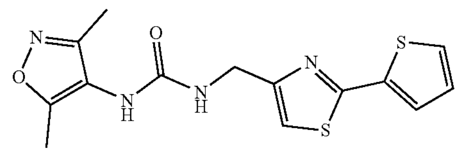 [SMILES: Cc1noc(C)c1NC(=O)NCc1csc(-c2cccs2)n1] | GAB-009 | NB | NB | ND | 38 | 162.9 ± 6.0 | 97.6 ± 6.1 |
| 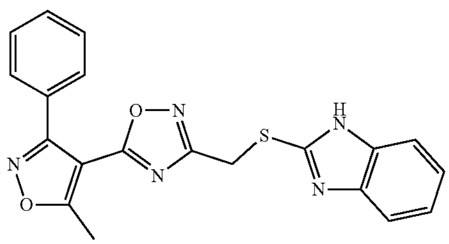 [SMILES: Cc1onc(-c2ccccc2)c1-c1nc(CSc2nc3ccccc3[nH]2)no1] | GAB-010 | NB | 0.12 ± 0.02 | ND | 92 | 66.0 ± 4.4 | 23.8 ± 4.2 |
| 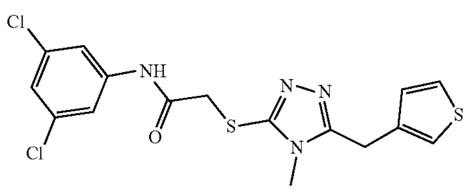 [SMILES: Cn1c(Cc2ccsc2)nnc1SCC(=O)Nc1cc(Cl)cc(Cl)c1] | GAB-011 | NB | NB | ND | 24 | IA | IA |
| 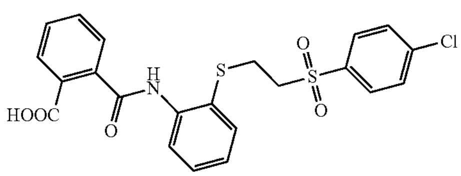 [SMILES: O=C(O)c1ccccc1C(=O)Nc1ccccc1SCCS(=O)(=O)c1ccc(Cl)cc1] | GAB-012 | NB | NB | 4.58 ± 1.72 | 43 | IA | 119.2 ± 3.6 |
| 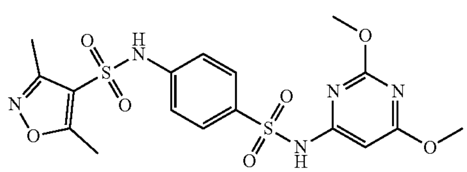 [SMILES: COc1cc(NS(=O)(=O)c2ccc(NS(=O)(=O)c3c(C)noc3C)cc2)nc(OC)n1] | GAB-013 | NB | NB | 6.27 ± 1.16 | 27 | IA | IA |
| 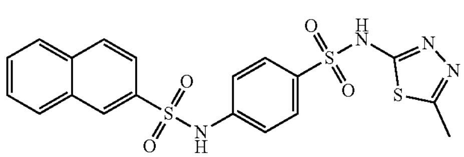 [SMILES: Cc1nnc(NS(=O)(=O)c2ccc(NS(=O)(=O)c3ccc4ccccc4c3)cc2)s1] | GAB-014 | NB | NB | NB | 42 | 69.9 ± 0.1** | 177.5 ± 3.9 |
| 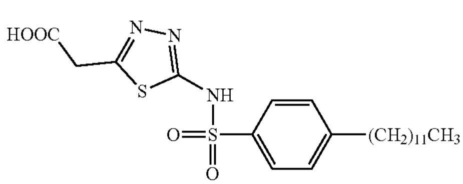 | GAB-015 | 13.1 ± 1.5* | 0.05 | 5.0 ± 0.4* | 77 | 71.7 ± 1.6 | 125.4 ± 5.4 |

TABLE 1-continued
Biochemical and biological activities of hits.
| Structure | ID | $K_n$ or $K_i$ (μM) | | | % pGAB1 in- hibition | IC$_{50}$ (μM) | |
| --- | --- | --- | --- | --- | --- | --- | --- |
| | | GAB1 | IRS1 | AKT1 | | MDA-MB-231 | T47D |
| 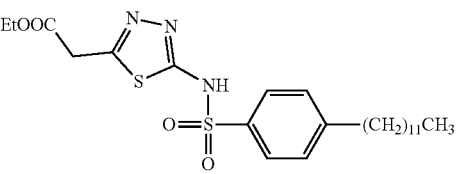 | GAB-016 | 0.9 ± 0.1 | 0.15 | 4.3 ± 0.1* | 96 | 79.0 ± 1.1 | 45.9 ± 1.6 |
| 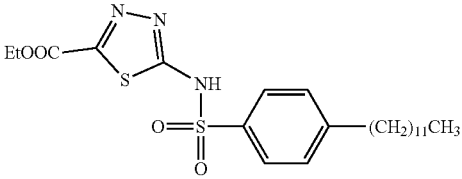 | GAB-017 | 0.68 ± 0.03 | 0.05 | 18.9 ± 1.2* | 82 | 40.6 ± 0.8 | 41.4 ± 2.7 |
| 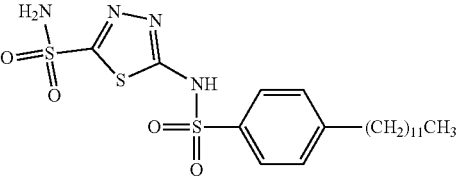 | GAB-018 | 36.6 ± 5.0* | NB | 6.0 ± 1.0* | 71 | 85.3 ± 1.5 | 185.4 ± 2.5 |
| 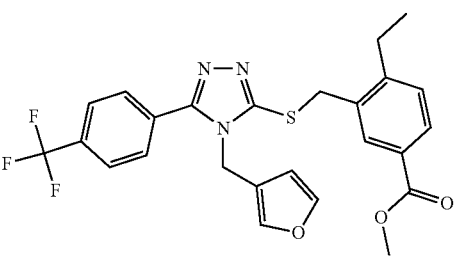 [SMILES: CCc1ccc(C(=O)OC)cc1CSc1nnc(-c2ccc(C(F)(F)F)cc2)n1Cc1ccoc1] | GAB-019 | ND | ND | ND | 91 | ND | 39.4 ± 6.2 |
| 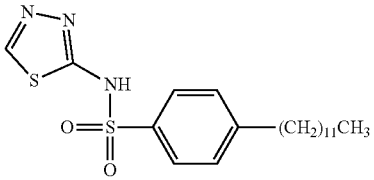 | GAB-020 | 1.33 ± 4.5 | ND | 2.4 ± 0.6* | 87 | ND | 68.2 ± 5.5 |

TABLE 1-continued

Biochemical and biological activities of hits.

| Structure | ID | $K_D$ or $K_i$ (μM) GAB1 | $K_D$ or $K_i$ (μM) IRS1 | $K_D$ or $K_i$ (μM) AKT1 | % pGAB1 inhibition | IC$_{50}$ (μM) MDA-MB-231 | IC$_{50}$ (μM) T47D |
|---|---|---|---|---|---|---|---|
| [structure] | DPIEL | 2.8 | ND | 5.04 ± 0.48 | 72 | ND | 30.6 ± 4.3 |
| [structure] | IP4 | ND | ND | 3.08 ± 0.49 | ND | ND | ND |

Note:
*Ki measurement.
**MDA-MB-468 cell line used.
ND: Not Determined.
NB: No Binding.
IA: Inactive Biological Evaluation of Identified Hits To validate the in silico identified hits, the inventors performed three types of experimental assays to evaluate their bioactivities: direct binding to GAB1 PH domain, inhibition of Y627 phosphorylation of GAB1, and cytotoxicity IC$_{50}$ in triple negative MDA-MB-231 and T47D human breast cancer cells. The experiments revealed that 10 out of 20 hits demonstrated submicromolar to micromolar binding affinity (<50 μM) to GAB1 PH domain measured by surface plasmon resonance (SPR). Among them, GAB-001, GAB-004, GAB-007, GAB-016 and GAB-017 demonstrated promising bioactivity in the subsequent in vitro assays (Table 1, FIG. 4 and FIG. 5).

GAB-001 exhibited selective binding to GAB1=9.4±1.6 μM) (FIG. 13), but not to IRS1 PH domain. In addition, it inhibited Y627 phosphorylation and killed breast cancer cells at IC$_{50}$=23.7±2.7 μM (for T47D). GAB-004 achieved similar binding selectivity as GAB-001, but had a stronger inhibition of pY627 (81%) and a lower IC$_{50}$ (19.4±2.9 μM). Interestingly GAB-007 demonstrated weak binding ($K_D$=42.3±8.9 μM) and mild pY627 inhibition (53%), but it showed high cytotoxicity in both MDA-MB-231 (IC$_{50}$=4.6±0.7 μM) and T47D (IC$_{50}$=20.1±4.3 μM) cell lines (FIG. 5), probably due to other off-target mechanisms. GAB-016 and GAB-017 are N-(1,3,4-thiadiazol-2-yl)benzenesulfonamide derivatives which were previously synthesized while searching for AKT PH domain inhibitors. They demonstrated nanomolar binding affinity for GAB1 PH domain (FIG. 13), and were 5-fold and 28-fold more selective to the GAB1 than AKT, respectively. Consistent to their high binding affinities, GAB-016 and GAB-017 also inhibited over 80% of Y627 phosphorylation.

GAB1 Targeted Tumor-Specific Cytotoxicity

Figure 5:
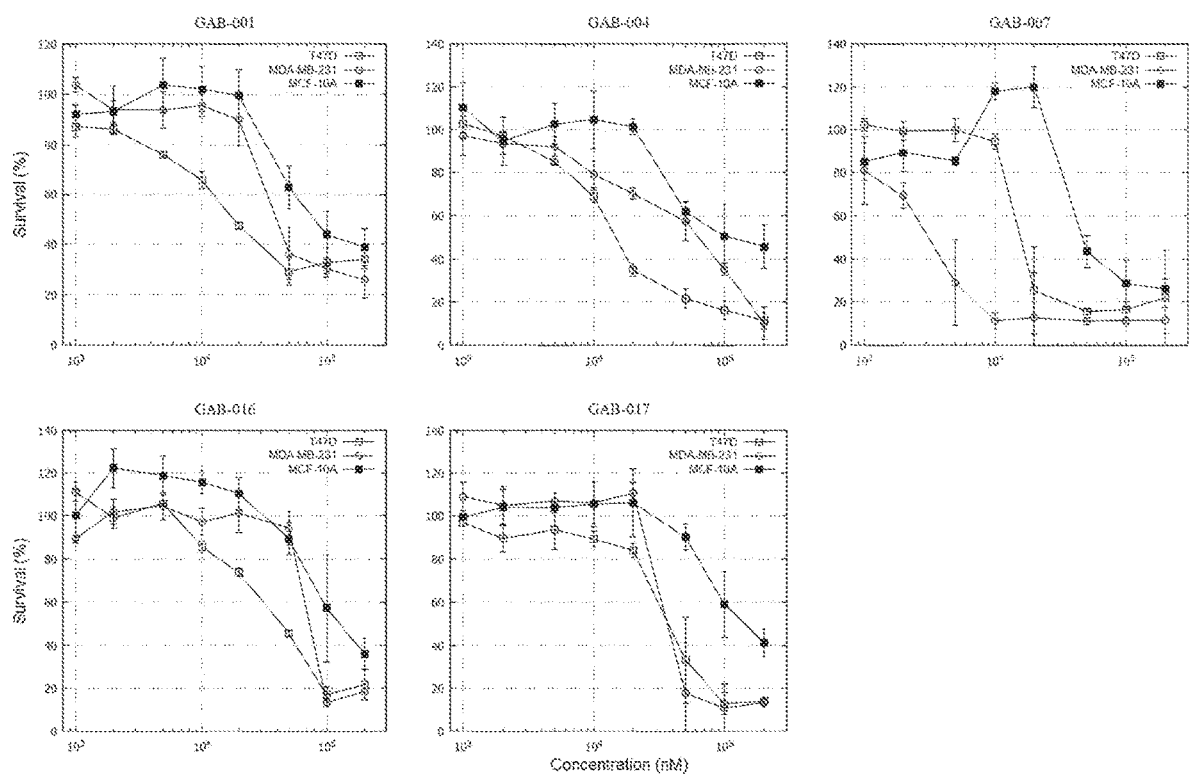
FIG. 5 shows a cell proliferation assay for T47D and MDA-MB-231 breast cancer cell line and MCF-10A breast epithelial cell line.
Figure 14:
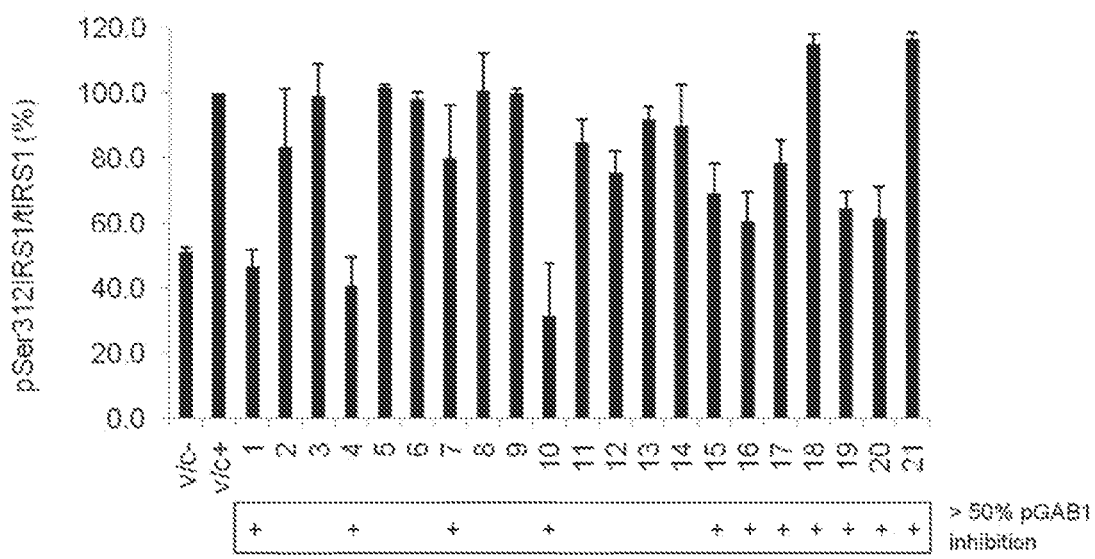
FIG. 14 shows inhibition of S312 phosphorylation of IRS1. The percentage of inhibition values are calculated from three separated experiments.

All the aforementioned active inhibitors showed potent cytotoxicity to cancer cell lines (T47D and MDA-MB-231). More excitingly, the cytotoxicity is specific to cancer cells as the inhibitors exhibit little inhibition in the non-cancer MCF-10A breast cell line (FIG. 5). Expectedly, as GAB1 and IRS1 pathways are intertwined, some inhibitors could suppress IRS1 phosphorylation (FIG. 14). In addition, some compounds that selectively bind AKT PH domain (e.g., GAB-012, GAB-013 and GAB-018) did not effectively kill MDA-MB-231 or T47D breast cancer cell lines at 50 μM (Table 1).

MD Simulation of Protein-Ligand Complexes and Binding Free Energy Calculation

Figure 15:
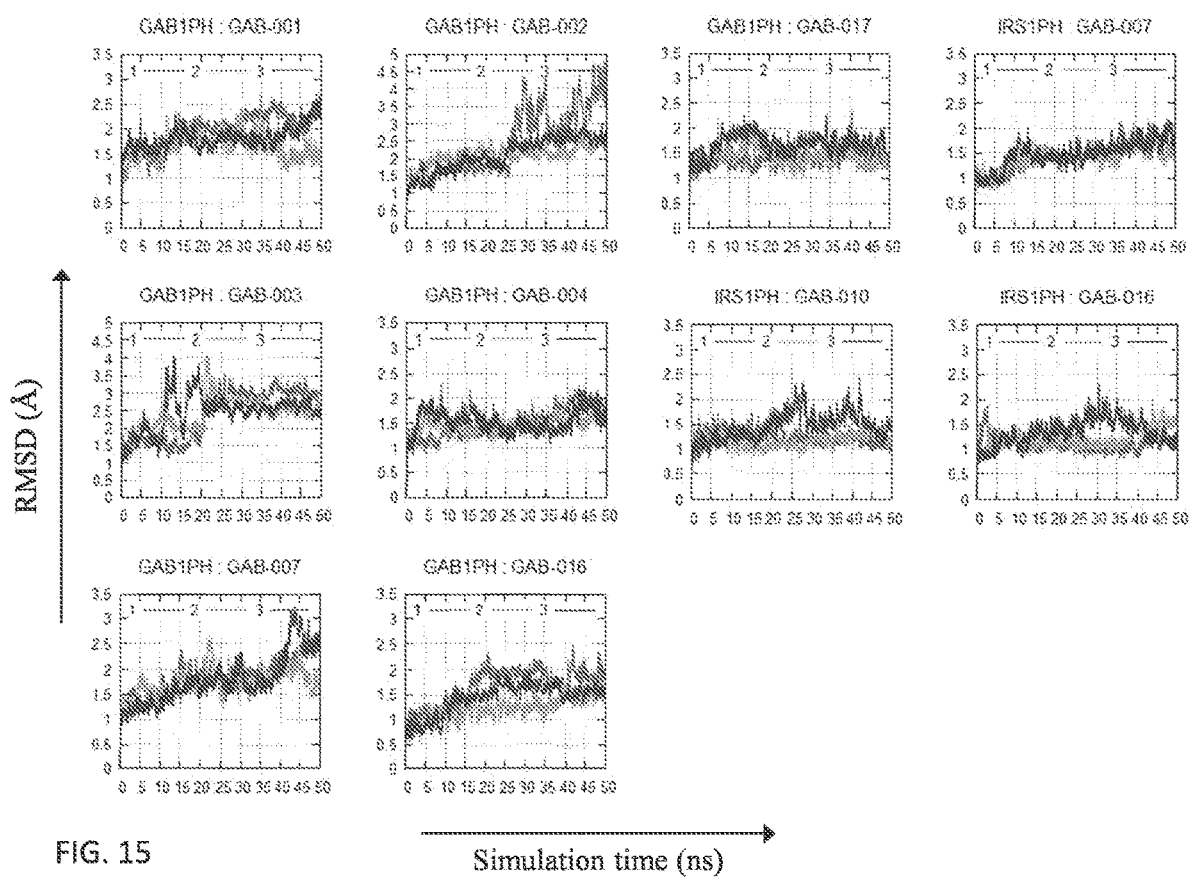
FIG. 15 shows a backbone RMSD of GAB1PH/IRS1PH-inhibitor complex.

To further investigate the structural mechanisms of the inhibitors to interact with the GAB1 PH domain, MD simulations of the protein-inhibitor complexes (listed in Table 2) were performed. As expected, the active compounds (GAB-001, GAB-004, GAB-007, GAB-016 and GAB-017) demonstrated stable bindings to GAB1 PH domain in three independent simulations (RMSD<2.5 Å), whereas GAB-002 and GAB-003 dissociated with the protein after around 25 ns (FIG. 15). In addition, MD simulations showed that GAB-007, GAB-010 and GAB-016 could form stable binding to IRS1 PH domain (FIG. 15), consistent to the SPR results in Table 1.

TABLE 2

Computation of the absolute binding free energy using PMF-based routine.

| | GAB1 | | | | |
|---|---|---|---|---|---|
| Component | GAB-001 | GAB-004 | GAB-007 | GAB-016 | GAB-017 |
| ΔGc, site (kcal/mol) | 1.14 | 0.98 | 0.92 | 1.42 | 1.31 |
| ΔGc, bulk (kcal/mol) | 1.27 | 1.00 | 1.09 | 1.52 | 1.65 |
| ΔGo, bulk (kcal/mol) | 1.04 | 0.9 | 0.85 | 0.98 | 0.67 |

TABLE 2-continued

Computation of the absolute binding free energy using PMF-based routine.

| $S^*$ (Å$^2$) | $6.27 \times 10^3$ | $8.74 \times 10^3$ | $9.94 \times 10^3$ | $7.00 \times 10^3$ | $7.91 \times 10^3$ |
|---|---|---|---|---|---|
| $I^*$ (Å) | $8.52 \times 10^5$ | $3.76 \times 10^5$ | $1.53 \times 10^4$ | $1.32 \times 10^7$ | $3.43 \times 10^6$ |
| $\Delta G_{bind}$ (kcal/mol) | −7.76 | −7.72 | −5.79 | −9.55 | −8.89 |
| Exp. $\Delta G_{bind}$ (kcal/mol) | −6.91 | −7.78 | −6.01 | −8.31 | −8.47 |

| | IRS1 | | |
|---|---|---|---|
| Component | GAB-007 | GAB-010 | GAB-016 |
| $\Delta G_c$, site (kcal/mol) | 1.02 | 0.84 | 1.26 |
| $\Delta G_c$, bulk (kcal/mol) | 1.08 | 1.07 | 1.46 |
| $\Delta G_o$, bulk (kcal/mol) | 1.14 | 0.85 | 0.94 |
| $S^*$ (Å$^2$) | $8.63 \times 10^3$ | $5.75 \times 10^3$ | $6.81 \times 10^3$ |
| $I^*$ (Å) | $1.04 \times 10^6$ | $1.18 \times 10^5$ | $4.90 \times 10^7$ |
| $\Delta G_{bind}$ (kcal/mol) | −8.05 | −9.36 | −10.26 |
| Exp. $\Delta G_{bind}$ (kcal/mol) | −7.93 | −9.51 | −9.38 |

Figure 6:
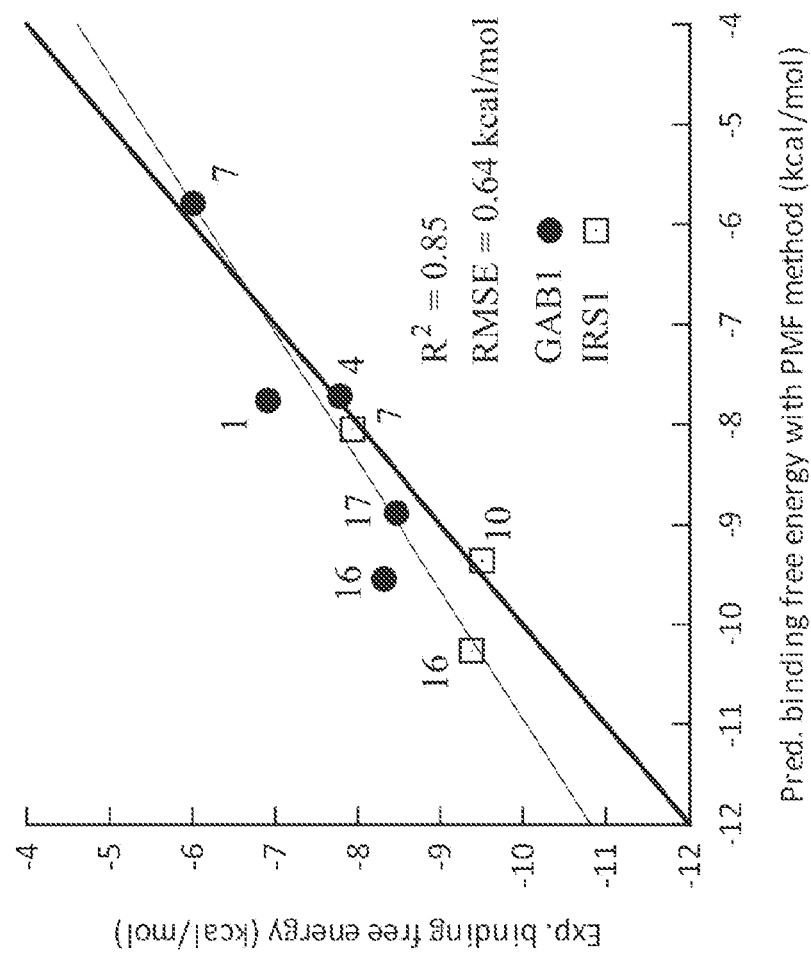
FIG. 6 shows a correlation between the predicted binding free energies (PMF method) and the experimental ones. The grey line indicates the calculated correlation between predicted and experimental binding free energies, and the black line indicates the ideal correlation. The number beside each point is the corresponding inhibitor ID.

To add another layer of validation of the binding modes predicted by MD simulations, the inventors calculated the absolute binding free energies of the inhibitors to GAB1/IRS1 PH domain using an in-house potential of mean force (PMF) method, which aims to circumvent the insufficient sampling issue by introducing hypothetical intermediate states representing the association pathway of ligand from the unbound "bulk" regions to the ligand-binding "site" (FIG. 16). The principle of this approach has been described elsewhere. Here, this method was implemented using ff99SB force field. Briefly, the umbrella sampling and weighted histogram analysis were used as the primary tools to derive two sets of PMF: ligand conformational PMF w(ξ) and protein-ligand separation PMF w(r). The details of mathematical calculations were described in the Results section, and the w(ξ) and w(r) plots for eight protein-ligand complexes were available in FIG. 17 and FIG. 18. As indicated by FIG. 6 and Table 2, the predicted absolute binding free energies via PMF method were in a good agreement with the experimental values (RMSE=0.64 kcal/mol, $R^2$=0.85). One may notice that these predictions encompassed two different PH domain targets (GAB1 and IRS1) and a variety of ligand chemotypes. The good correlation between experimental binding free energies and predicted free energies implied that the predicted inhibitor binding modes by MD simulations were accurate.

Ligand-Induced Conformational Changes of PH Domain

The inventors have generated eight reliable PH domain-inhibitor complex models from MD simulations (listed in Table 2) which have been validated by the PMF absolute binding free energy calculations as described herein. When comparing the bound and unbound protein structures, it was observed for the first time the ligand-induced conformational changes in three regions around the phosphoinositide-binding pocket (termed as Region I, Region II and Region III) for both GAB1 and IRS1 PH domains.

Figure 7A:
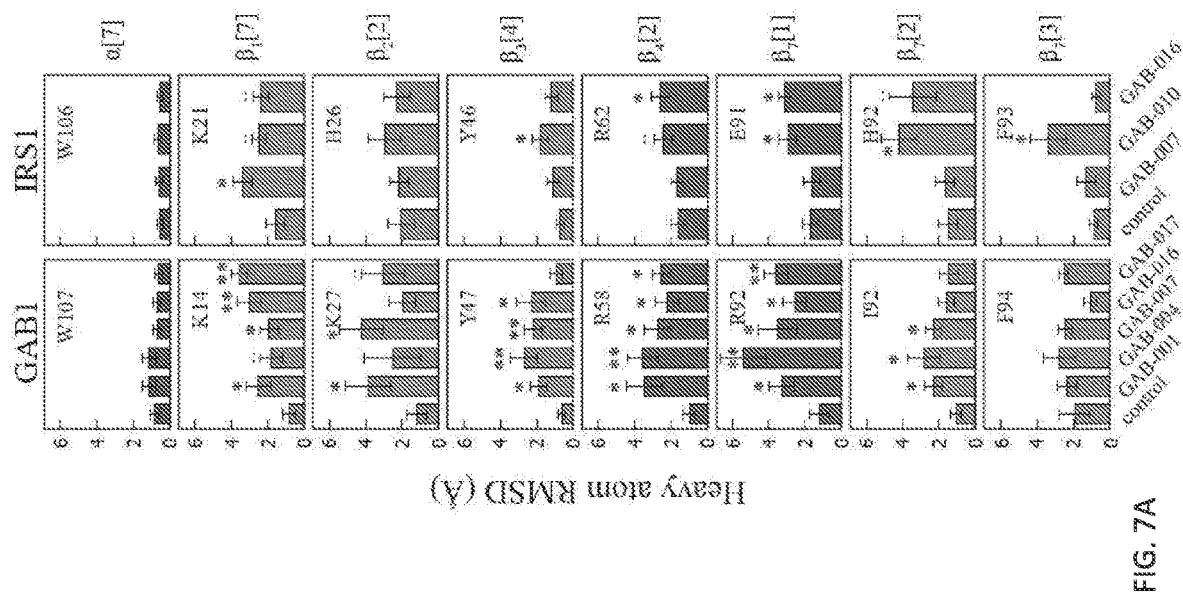
FIGS. 7A-7E show inhibitor-induced conformational changes for PH domain structures.
Figure 7B:
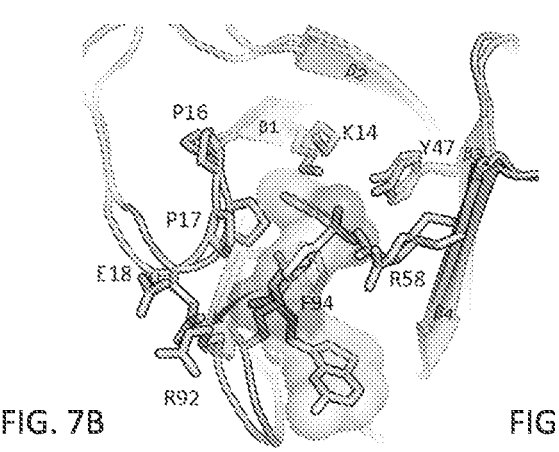
Figure 7C:
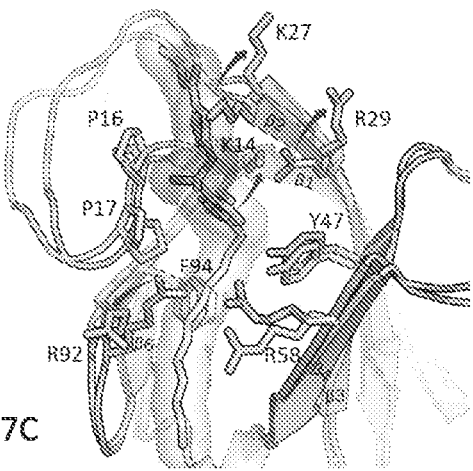
Figure 7D:
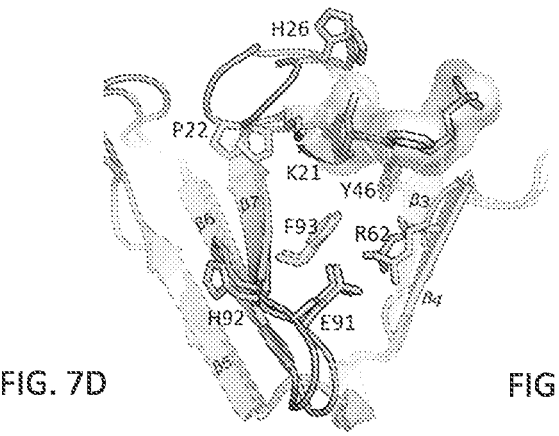
Figure 7E:
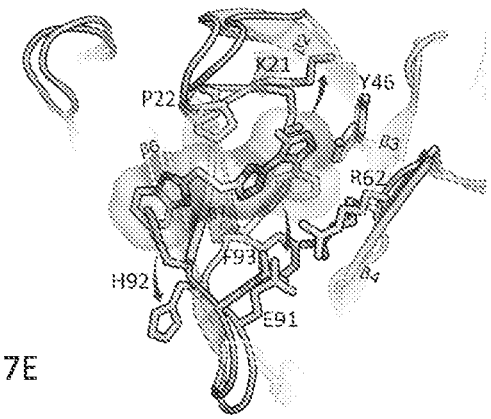
Figure 19:
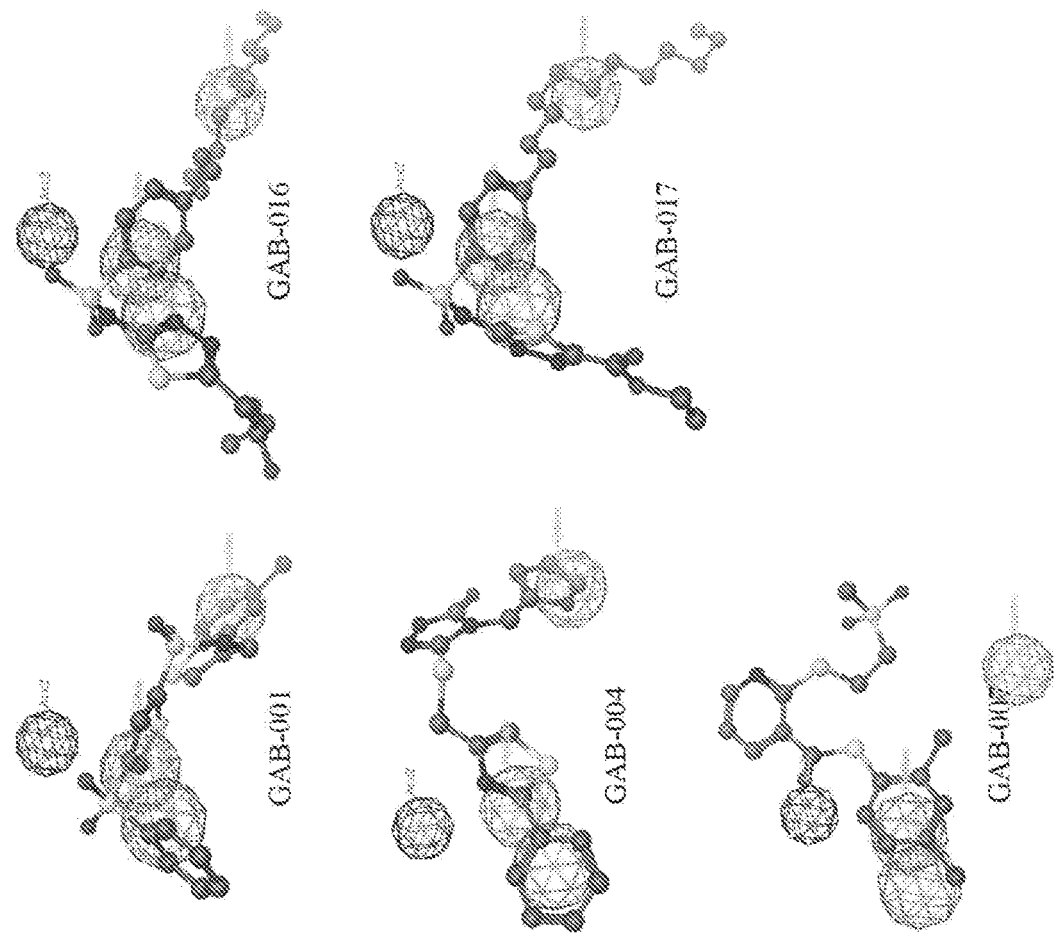
FIG. 19 shows a pharmacophore of the inhibitors. The green represents a hydrophobic or aromatic region. The blue represents a projection of H-bond acceptor.

The Region I is comprised of the conserved $K14_{GAB1}/K21_{IRS1}$ ($\beta_1[7]$), $K27_{GAB1}/K21_{IRS1}$ ($\beta_2[2]$), $Y47_{GAB1}/Y46_{IRS1}$ ($\beta_3[4]$) and $F94_{GAB1}/F93_{IRS1}$ ($\beta_7[3]$) (FIG. 7A-E). The MD simulations showed significant conformational changes in Region I (RMSD>2A) for both GAB1 and IRS1, as illustrated by the RMSD analysis (red plots in FIG. 7A). The side chain rearrangement of these residues, especially $K14_{GAB1}/K21_{IRS1}$ and $Y47_{GAB1}/Y46_{IRS1}$, created a pocket which favorably binds an aromatic moiety connecting with a H-bond acceptor group. This moiety could form cation-π and hydrophobic interactions with the surrounding $K14_{GAB1}/K21_{IRS1}$ and $F94_{GAB1}/F93_{IRS1}$, respectively (FIG. 7B-7E). All inhibitors identified in this study contain such a pharmacophore (phenylthiazole in GAB-004, phenylisoxazole in GAB-010, S-phenyl carbothioate in GAB-007, benzenesulfone in GAB-001, GAB-016 and GAB-017) (FIG. 19). As previously mentioned, the $\beta_1[7]$, $\beta_2[2]$ and $\beta_3[4]$ were the PIP3-binding residues, thus Region I conformational changes were attributable to the activities of the inhibitors. Generally, the conformational changes of Region I residues in GAB1 were more substantial than IRS1, except $F94_{GAB1}$ (FIG. 7A). In comparison, GAB-010 could induce an alternative conformation of $F93_{IRS1}$ (FIG. 7E), which also occurred in ArhGAP9 crystal structure (PDB ID: 2P0D). The function of conformational change of $F93_{IRS1}$ is likely to further open the pocket to accommodate larger moiety such as phenylisoxazole (GAB-010), as other IRS1 Region I residues were less flexible.

The Region II is formed by $\beta_4$, $\beta_{6,7}$ loop and the first several amino acids of $\beta_7$ (FIG. 7A-E). The key residues are $R58_{GAB1}/R62_{IRS1}$ ($\beta_4[2]$) and $R92_{GAB1}/E91_{IRS1}$ ($\beta_7[1]$). Compared with Region I residues, more significant conformational changes were observed in the Region II residues in the GAB1 PH domain (RMSD>2.5 Å) (blue plots in FIG. 7A). These conformational changes created a new pocket which binds aliphatic (GAB-016 and GAB-017) and aromatic moieties (e.g., chlorobenzothiophene in GAB-001 and furan in GAB-004). Remarkably, the bulky aromatic moieties (GAB-001 and GAB-004) generally induced more movement of GAB1 Region II residues than the aliphatic moieties (GAB-016 and GAB-017) (blue plots in FIG. 7A). It was also observed that significant conformational changes only occurred in GAB1, but not in IRS1 PH domain (blue plots in FIG. 7A), probably because the electrostatic attraction between $R62_{IRS1}$ and $E91_{IRS1}$ significantly restrained the fluctuation of these two residues, while the electrostatic repelling between $R58_{GAB1}$ and $R92_{GAB1}$ made these two residues more flexible. These findings imply that the flexibility of Region II residues of PH domain may correlate the size of binding group.

The Region III is located on the solvent-accessible side of the $\beta_7$, especially $I92_{GAB1}$ or $H92_{IRS1}$ ($\beta_7[3]$) (FIG. 7A-E). When GAB-010 binds IRS1 PH domain, the benzimidazole moiety induced a significant side chain movement of H92 (RMSD=3.39 Å) as compared with unbound form (magenta plots on the right in FIG. 7A. In contrast, this region in GAB1 PH domain did not exhibit significant conformational changes when binding any inhibitor (magenta plots on the left in FIG. 7A). Upon comparison of GAB1 and IRS1 PH domain sequences, it is speculated that the accessibility of Region III was affected by the length of $\beta_{1,2}$ loop: GAB1 PH domain has a longer $\beta_{1,2}$ loop than IRS1 (FIG. 2), and the residues P16 and P17 forms intensive vdW interactions with $\beta_7$, which would in turn block the access of inhibitors to Region III. This explains the selective binding of GAB-010 to IRS1, but not GAB1 PH domain.

TABLE 3

Docking scores for 20 hits. The hits which are consistently active in three assays are labeled with bold IDs.

| Compound ID | Structure | ChemPLP |
|---|---|---|
| GAB-001 | 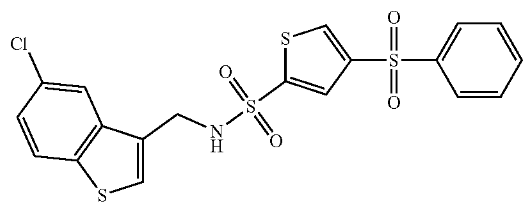 [SMILES: O=S(=O)(NCc1csc2ccc(Cl)cc12)c1cc(S(=O)(=O)c2ccccc2)cs1] | 83.87 |
| GAB-002 | 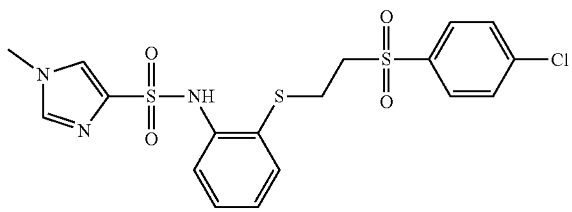 [SMILES: Cn1cnc(S(=O)(=O)Nc2ccccc2SCCS(=O)(=O)c2ccc(Cl)cc2)c1] | 78.18 |
| GAB-003 | 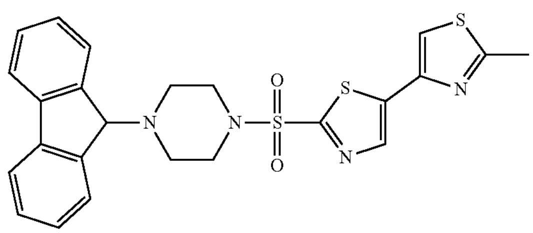 [SMILES: Cc1nc(-c2cnc(S(=O)(=O)N3CCN(C4c5ccccc5-c5ccccc54)CC3)s2)cs1] | 81.7 |
| GAB-004 | 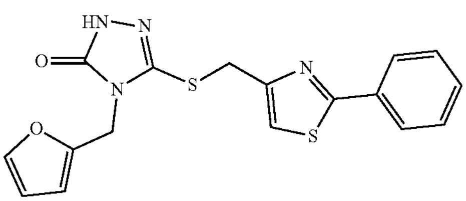 [SMILES: O=c1[nH]nc(SCc2csc(-c3ccccc3)n2)n1Cc1ccco1] | 75.44 |
| GAB-005 | 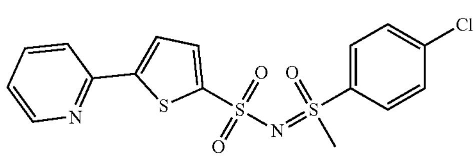 [SMILES: CS(=O)(=NS(=O)(=O)c1ccc(-c2ccccn2)s1)c1ccc(Cl)cc1] | 80.45 |
| GAB-006 | 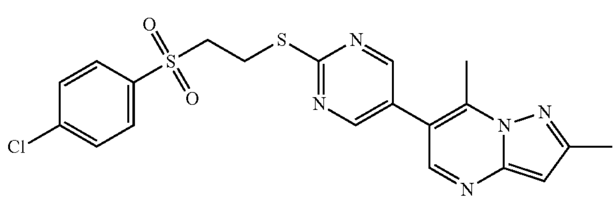 [SMILES: Cc1cc2ncc(-c3cnc(SCCS(=O)(=O)c4ccc(Cl)cc4)nc3)c(C)n2n1] | 82.91 |
| GAB-007 | 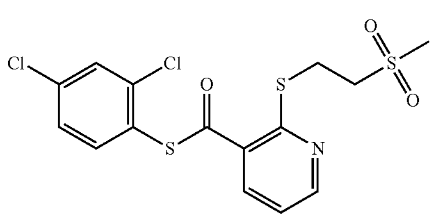 [SMILES: CS(=O)(=O)CCSc1ncccc1C(=O)Sc1ccc(Cl)cc1Cl] | 78.68 |

TABLE 3-continued

Docking scores for 20 hits. The hits which are consistently active in three assays are labeled with bold IDs.

| Compound ID | Structure | ChemPLP |
|---|---|---|
| GAB-008 | 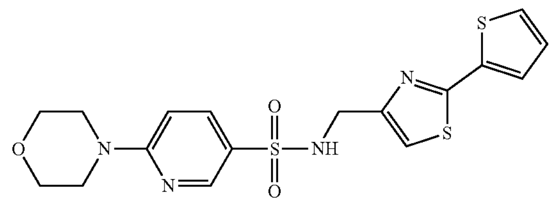 [SMILES: O=S(=O)(NCc1csc(-c2cccs2)n1)c1ccc(N2CCOCC2)nc1] | 75.72 |
| GAB-009 | 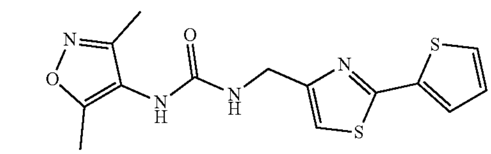 [SMILES: Cc1noc(C)c1NC(=O)NCc1csc(-c2cccs2)n1] | 73.3 |
| GAB-010 | 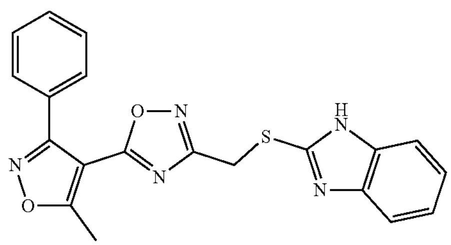 [SMILES: Cc1onc(-c2ccccc2)c1-c1nc(CSc2nc3ccccc3[nH]2)no1] | 79.14 |
| GAB-011 | 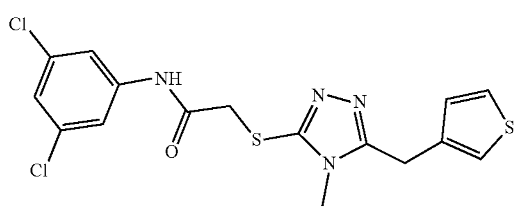 [SMILES: Cn1c(Cc2ccsc2)nnc1SCC(=O)Nc1cc(Cl)cc(Cl)c1] | 75.34 |
| GAB-012 | 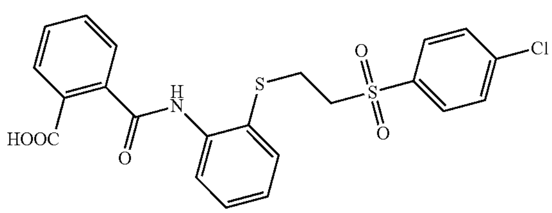 [SMILES: O=C(O)c1ccccc1C(=O)Nc1ccccc1SCCS(=O)(=O)c1ccc(Cl)cc1] | 82.3 |
| GAB-013 | 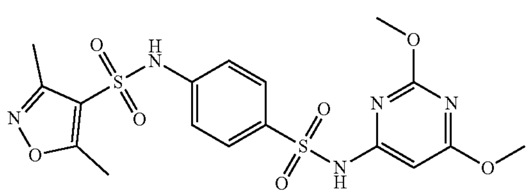 [SMILES: COc1cc(NS(=O)(=O)c2ccc(NS(=O)(=O)c3c(C)noc3C)cc2)nc(OC)n1] | 62.42 |
| GAB-014 | 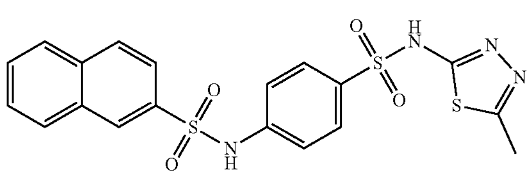 [SMILES: Cc1nnc(NS(=O)(=O)c2ccc(NS(=O)(=O)c3ccc4ccccc4c3)cc2)s1] | 80.07 |

TABLE 3-continued

Docking scores for 20 hits. The hits which are consistently active in three assays are labeled with bold IDs.

| Compound ID | Structure | ChemPLP |
|---|---|---|
| GAB-015 | 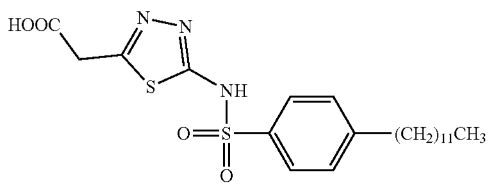 | 82.98 |
| GAB-016 | 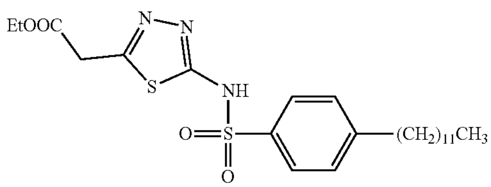 | 89.07 |
| GAB-017 | 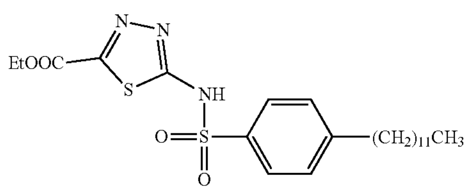 | 88.24 |
| GAB-018 | 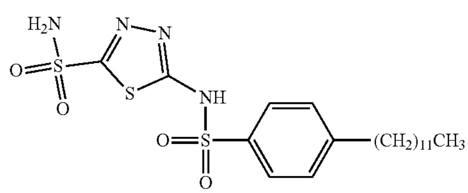 | 85.26 |
| GAB-019 | 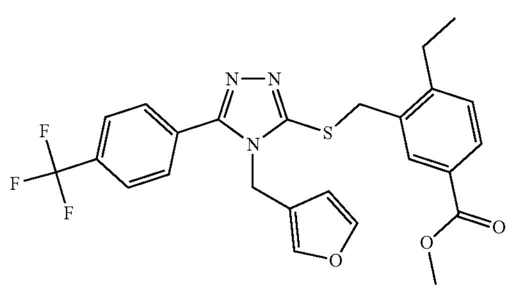 [SMILES: CCc1ccc(C(=O)OC)cc1CSc1nnc(-c2ccc(C(F)(F)F)cc2)n1Cc1ccoc1] | 103.92 |
| GAB-020 | 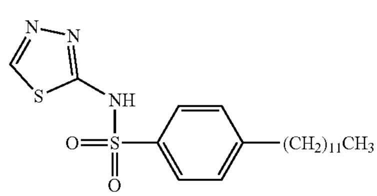 | 83.18 |
| DPIEL | 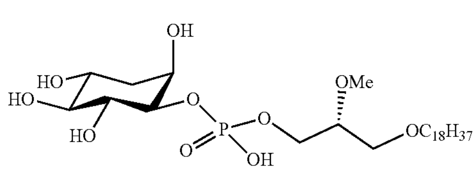 | NA |

TABLE 3-continued

Docking scores for 20 hits. The hits which are consistently active in three assays are labeled with bold IDs.

| Compound ID | Structure | ChemPLP |
|---|---|---|
| IP4 | [chemical structure] | NA |

TABLE 4

The crystal structures employed to generate PSSM.

| PDB ID | Protein name |
|---|---|
| 3UZT | GRK2 |
| 1EAZ | TAPP1 |
| 1FAO | DAPP1 |
| 1WID | PDPK1 |
| 1U27 | ARNO |
| 1FHW | GRP1 |
| 1UPR | Pepp1 |
| 3AJ4 | Evectin-2 |
| 4FJH | Kindlin-2 |
| 2DYN | Dynamin-1 |
| 2DTC | RalGPS1 |
| 3PP2 | ArbGAP27 |
| 2P0H | ArbGAP9 |
| 3NSU | SLM1 |
| 3CXB | SKIP |
| 3HK0 | Grb10 |
| 1QQG | IRS1 |
| 1UNQ | AKT1 |
| 1XD4 | SOS homolog 1 |
| 1LB1 | Dbs |
| 2KZ1 | PRG |
| 1KI1 | Intersectin |
| 1FOE | Tiam1 |
| 2W2X | PLCG2 |
| 2VSZ | ELMO1 |
| 1MAI | PLCD1 |
| 3TW1 | Rtt1066 |
| 2R2Y | Rpn13 |
| 3VOQ | Sin1 |
| 3U12 | USP37 |
| 3PEG | Neurofibromin |
| 4EMO | SHARPIN |
| 4DIX | SCAB1 |
| 3RCP | Papp1 |

TABLE 5

PSSM profile for PH domain (β1, β2, β3, β6, β7, and α1).

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| β1 | | | | | | | | | | | | | | | | | | | | |
| | -2 | -2 | -2 | -2 | 0 | 1 | -2 | 0 | -1 | 2 | 0 | 0 | 0 | 1 | 1 | 3 | -2 | -2 | -3 | 1 | 1 |
| | -1 | -1 | 1 | -1 | 1 | -3 | 1 | 1 | -3 | 2 | 0 | 0 | 1 | -1 | -2 | 0 | 1 | -2 | 2 | 0 |
| | 1 | -1 | 0 | -2 | -2 | 3 | 1 | 1 | -3 | 3 | 0 | 0 | 3 | 2 | 0 | -3 | -1 | -2 | -3 | -2 | 1 |
| | 2 | 1 | -1 | -1 | 0 | 3 | 1 | 2 | 3 | 2 | -3 | -3 | 1 | 0 | 0 | -3 | 1 | 0 | -4 | -2 | -2 |
| | 3 | -2 | -3 | -2 | 0 | -4 | -3 | -1 | 4 | 1 | 0 | -1 | -3 | -2 | 2 | 0 | 0 | -1 | -3 | -2 | 0 |
| | 4 | -2 | -1 | 1 | -3 | 1 | 0 | -2 | -4 | 3 | -2 | 1 | 0 | 1 | 1 | 0 | -1 | -1 | 4 | 3 | 0 |
| | 5 | 0 | -1 | -1 | -4 | 2 | -3 | -3 | -1 | 1 | 2 | 2 | -3 | 1 | 1 | -4 | -2 | -2 | -3 | 1 | 1 |
| | 6 | -1 | 2 | -2 | -1 | -3 | -1 | -1 | -1 | 4 | -2 | 0 | 0 | 2 | -2 | 1 | 1 | 0 | 4 | 0 | 0 |
| | 7 | -3 | 2 | -3 | -4 | -4 | -2 | -2 | -4 | -3 | 1 | 0 | 4 | 1 | -3 | -4 | -3 | 1 | 4 | 0 | 2 |
| | 8 | -1 | 3 | -1 | 0 | -3 | 1 | -1 | -1 | -2 | 0 | 0 | 2 | 2 | 0 | -1 | -2 | 0 | 3 | -2 | 0 |
| β2 | | | | | | | | | | | | | | | | | | | | |
| | 1 | -1 | 1 | 1 | 2 | -4 | -2 | 0 | -3 | 2 | -4 | -4 | -2 | -3 | -2 | 0 | -1 | 1 | 9 | 2 | -4 |
| | 2 | 0 | 1 | -2 | -2 | -4 | 0 | -1 | -1 | -2 | -3 | -2 | 5 | 0 | 0 | 1 | 1 | 1 | -4 | -3 | -3 |
| | 3 | -1 | 3 | -1 | 1 | -4 | 2 | -3 | 1 | -1 | 3 | -2 | -1 | 1 | -1 | -1 | -4 | -2 | -3 |
| | 5 | -2 | 3 | -1 | -3 | 0 | -2 | -2 | 1 | 3 | -2 | 1 | -1 | -1 | 1 | -3 | 0 | -2 | 3 | 2 | 0 |
| | 6 | -1 | 0 | -3 | -4 | -4 | -3 | -3 | -4 | 4 | -3 | 0 | -3 | -2 | 3 | -4 | 0 | -1 | 8 | 4 | -3 |
| | 7 | -1 | -4 | -4 | 4 | 4 | -3 | -4 | -2 | -3 | 1 | 2 | -4 | 0 | 4 | -4 | -3 | -1 | -2 | 1 | 2 |
| | 8 | -1 | 0 | -2 | -1 | 0 | 0 | -1 | -1 | 1 | 0 | 1 | 0 | -1 | 3 | -3 | -2 | 0 | -2 | 2 | 1 |
| | 9 | -3 | 0 | -5 | -5 | -3 | -4 | -4 | -5 | -4 | 3 | 4 | -3 | 0 | 2 | -4 | -4 | -2 | -3 | -2 | 2 |
| β3 | | | | | | | | | | | | | | | | | | | | |
| | 1 | 1 | 1 | 1 | -1 | -3 | 2 | -1 | -1 | -1 | 3 | 0 | 0 | 0 | -2 | 0 | -3 | 1 | 1 | -3 | -2 | 0 |
| | 2 | -3 | -1 | -5 | -6 | -3 | -4 | -5 | -6 | -5 | 3 | 4 | -4 | 2 | 2 | -5 | -4 | -3 | -4 | -2 | 3 |
| | 3 | -2 | -2 | -3 | -3 | 2 | 0 | 1 | -2 | 2 | 2 | 1 | -1 | -1 | 0 | -3 | 0 | -1 | 3 | 3 | 1 |
| | 4 | -3 | -4 | -4 | -4 | 5 | 1 | 0 | -2 | -3 | 0 | 1 | -4 | -2 | -3 | -5 | -3 | -3 | 6 | 2 | 0 |

TABLE 5-continued

PSSM profile for PH domain (β1, β2, β3, β6, β7, and α1).

|     | A  | R  | N  | D  | C  | Q  | E  | G  | H  | I  | L  | K  | M  | F  | P  | S  | T  | W  | Y  | V  |
|-----|----|----|----|----|----|----|----|----|----|----|----|----|----|----|----|----|----|----|----|----|
| 5   | -2 | -1 | -3 | 0  | 4  | -1 | -1 | -1 | 1  | -3 | -2 | 0  | -2 | 3  | -4 | 0  | 0  | -2 | -2 | -1 |
| +1  | -2 | 0  | -2 | 2  | -5 | 0  | 0  | 0  | -2 | -4 | -4 | 4  | -3 | 0  | 1  | 1  | 0  | -3 | 3  | -4 |

β6

|     | A  | R  | N  | D  | C  | Q  | E  | G  | H  | I  | L  | K  | M  | F  | P  | S  | T  | W  | Y  | V  |
|-----|----|----|----|----|----|----|----|----|----|----|----|----|----|----|----|----|----|----|----|----|
| 1   | 0  | 1  | 1  | -2 | 3  | 1  | -1 | 0  | -2 | 1  | 0  | 1  | 2  | -2 | -3 | -1 | 1  | -3 | -2 | 0  |
| 2   | -2 | -4 | -5 | -5 | 1  | -4 | -5 | 0  | 1  | 0  | 3  | -5 | -1 | 7  | -5 | -4 | -3 | 2  | 2  | 0  |
| 3   | 0  | -2 | -2 | -2 | 2  | 1  | 2  | 3  | 2  | 0  | 0  | 0  | -1 | 1  | -3 | 0  | 1  | -2 | 2  | 0  |
| 4   | 0  | -4 | -5 | -5 | -3 | -4 | -4 | -3 | 4  | 4  | 4  | -4 | 0  | -2 | -4 | -3 | 0  | 3  | -2 | 1  |
| 8   | -2 | 1  | 0  | -2 | -3 | 2  | 1  | -3 | 1  | 1  | 0  | 1  | -1 | 0  | -3 | -1 | 0  | 2  | 1  | 1  |

β7

|     | A  | R  | N  | D  | C  | Q  | E  | G  | H  | I  | L  | K  | M  | F  | P  | S  | T  | W  | Y  | V  |
|-----|----|----|----|----|----|----|----|----|----|----|----|----|----|----|----|----|----|----|----|----|
| 1   | -2 | 2  | 2  | -2 | 2  | 1  | 2  | -3 | 3  | -1 | -3 | 2  | 0  | -4 | 3  | 0  | -2 | -3 | -3 | 0  |
| 2   | -2 | 0  | 1  | -2 | 1  | 1  | 2  | 0  | 2  | -1 | -1 | -1 | -2 | 0  | 1  | 0  | 1  | -4 | -2 | 1  |
| 3   | -4 | 1  | -5 | -5 | -4 | -4 | -4 | -3 | -3 | 1  | 2  | -4 | -2 | 4  | -3 | -4 | 0  | 4  | 5  | 0  |
| 4   | -1 | 0  | 0  | -1 | -3 | -1 | 1  | -3 | 0  | 0  | 1  | -1 | -1 | 0  | -3 | 0  | 1  | 3  | 2  | 1  |
| 5   | -3 | -5 | -5 | -4 | -5 | -5 | -5 | -4 | 3  | 3  | 3  | -5 | -1 | 6  | -5 | -1 | -3 | -3 | -1 | 0  |
| 6   | 0  | 0  | -2 | 0  | 4  | 2  | 0  | -3 | 3  | -1 | -2 | 0  | 2  | -3 | 3  | 1  | -1 | 4  | -2 | -1 |
| +1  | 3  | -3 | -2 | 0  | 4  | -2 | -2 | -2 | 2  | 0  | -2 | -2 | 2  | 1  | -3 | 0  | 1  | -3 | -2 | 0  |
| +2  |    | -2 | -1 | 4  | -4 | 2  | 2  | 0  | -2 | -4 | -1 | 0  | -2 | -4 | 3  | 0  | -2 | -4 | -3 | -1 |

α1

|     | A  | R  | N  | D  | C  | Q  | E  | G  | H  | I  | L  | K  | M  | F  | P  | S  | T  | W  | Y  | V  |
|-----|----|----|----|----|----|----|----|----|----|----|----|----|----|----|----|----|----|----|----|----|
| 1   | -2 | -2 | 2  | 2  | -4 | -2 | -2 | -3 | 3  | -4 | -4 | 2  | -3 | -4 | 2  | 3  | 3  | -5 | -3 | -4 |
| 2   | 0  | 1  | -1 | 0  | -2 | 1  | 0  | 0  | -1 | 0  | -1 | 0  | -1 | -2 | 1  | 0  | 0  | -2 | 1  | 0  |
| 3   | 1  | -1 | 0  | 1  | -3 | 1  | 3  | -3 | 2  | -3 | -3 | 1  | -3 | 0  | 0  | 0  | 0  | -4 | -2 | -2 |
| 4   | -3 | -2 | 1  | 3  | -5 | 2  | 5  | -4 | 3  | 1  | -4 | -2 | -3 | -3 | 1  | 0  | -5 | -4 | -3 | 0  |
| 5   | 2  | 2  | -3 | -1 | 2  | 0  | -2 | -3 | -2 | 0  | 1  | 1  | 2  | -2 | -3 | -2 | -2 | -3 | 1  | 0  |
| 6   | 0  | 0  | 1  | 1  | 1  | 1  | 1  | 2  | 2  | 0  | -1 | 0  | 1  | -1 | -2 | 0  | 0  | -3 | -2 | -1 |
| 7   | 1  | 0  | 0  | 0  | -3 | 1  | 2  | -1 | 2  | -1 | -1 | 1  | -2 | -3 | -2 | 1  | 1  | -4 | -2 | -2 |
| 8   | -1 | -6 | 6  | -7 | -5 | -5 | -6 | -6 | 2  | 1  | -4 | -6 | -4 | 1  | -6 | -5 | -6 | 11 | -1 | -4 |
| 9   | -1 | 0  | -2 | -1 | 2  | -2 | -2 | -4 | 2  | 2  | 0  | 0  | 4  | 1  | -3 | -2 | 0  | -3 | 0  | 1  |
| 10  | 0  | 2  | 0  | 1  | -3 | 2  | 0  | -3 | -2 | -2 | 0  | 2  | 1  | 0  | -2 | -1 | 0  | -3 | -2 | 0  |
| 11  | 2  | -2 | 0  | -2 | -2 | -1 | 0  | 0  | 1  | -1 | 0  | 1  | -1 | 0  | -2 | 1  | 0  | -3 | 1  | -1 |
| 12  | 0  | -4 | -5 | -3 | 1  | -4 | -4 | -3 | -4 | 3  | 4  | -4 | 0  | 1  | -4 | -3 | -2 | -3 | -2 | 3  |
| 13  | -1 | 4  | 2  | 1  | 0  | 2  | 0  | -1 | 1  | -1 | -1 | 2  | -2 | -4 | -3 | -1 | -2 | -4 | -3 | -3 |
| 14  | 1  | 2  | -1 | 1  | -3 | 2  | 1  | 0  | 0  | -1 | -1 | 1  | -2 | -2 | -2 | 0  | 0  | 2  | 0  | -2 |
| 15  | 2  | -2 | -3 | -3 | 1  | -2 | -3 | -1 | -3 | 2  | 1  | 0  | -1 | 1  | -3 | 0  | -1 | -3 | -2 | 2  |

GAB1 is a critical protein in cellular signaling, and its PH domain has been suggested as an attractive target for various cancer treatments. However, the absence of its 3D structure makes it challenging for structure-based drug discovery. Herein, the present invention features a rigorously designed workflow for inhibitor identification by integrating various techniques ranging from structural bioinformatics, homology modeling, ligand-steered refinement, molecular dynamics, and virtual screening, followed by experiment evaluation with biochemical/biophysical and cellular assays. With the integrated protocol, several selective inhibitors have been successfully identified targeting the GAB1 PH domain and they are selective to breast cancer cells. This discovery offers a great starting point to target this critical protein for cancer treatment, particularly for the triple negative breast cancer.

The results also showed that the triple-negative breast cancer cell line, MDA-MB-231, was more resistant to GAB1 inhibitors than ER-positive breast cancer cell line, T47D (Table 1). It has been reported that MDA-MB-231, but not T47D, has mutations on GAB1 downstream proteins, such as KRas and BRaf mutations. Since KRas and BRaf mutations are known to reduce the dependency on the upstream activators, such as EGFR, it was not surprising that MDA-MB-231 was more resistant to GAB1 inhibitors. Strikingly, it was observed a concomitant inhibition of pGAB1 and pIRS1 by either GAB1-specific or IRS1-specific inhibitors (FIG. 14). This could be due to the crosstalk between c-Met and α6β4 integrin pathway, which couples the phosphorylation of GAB1 and IRS1 upon HGF stimulation. These observations may bring new insights of combined PH domain-targeted cancer therapeutic strategies.

Although selective inhibitors of the GAB1 PH domain have been identified using the unique computation-experimentation integrated platform, the inventors further disclose that some of the other hits also bind to multiple PH domains (e.g., IRS1 and AKT1), as demonstrated by Table 1. For example, GAB-001 and GAB-004 are selectively inhibitor GAB1, but GAB-016 and GAB-017 are pan inhibitors against GAB1, SRS1 and AKT1. More follow-up experiments also showed that GAB-016 targets GAB2 PH domain as well. In addition, GAB1 and GAB2 PH domains are highly homologous (76% sequence identity), and IRS1 is one of the templates used in the homology modeling to build the 3D structure of GAB1 PH domain. Of note, all GAB1-selective or IRS1-selective inhibitors showed much better $IC_{50}$ against T47D and MDA-MB-231 breast cancer cell lines than the non-tumorigenic MCF-10A cell line (FIG. 5). More intriguingly, it is also observed that AKT1-selective inhibitors (e.g., GAB-012 and GAB-013) were toxic to MCF-10A at 100 μM, but not for T47D and MDA-MB-231 at the same concentration (data not shown). This may imply that targeting GAB1 or 8RS1, but not AKT1, might be a better targeted strategy for breast cancer treatment.

Although PH domains have been intensively studied as cancer target for drug discovery, to date there are no available protein structures in complex with any drug-like small molecules. As mentioned, this has significantly limited the structure-based drug discovery efforts. In the present invention, several inhibitors were utilized to investigate the dynamics of GAB1 PH domain and evaluate their selectivity in potential cancer cell inhibition. Interestingly, it was found that the apo-structure of the PH domain protein could undergo large conformational changes in three regions to accommodate different inhibitors. The side-chain conformations of the residues in Region I determines the binding of either multiple electronegative groups (e.g., the multiple phosphates in IP4) or an aromatic moiety conjugated with a group containing H-bond acceptors (e.g., benzenesulfone), as shown in FIG. 7. The accessibility of Region II and Region III depend on several critical amino acids on $\beta_4$ and $\beta_7$ and the length of $\beta_{1,2}$ loop, respectively. The selectivity of PH domain inhibitors may be designed based on the modeling of the protein structures. For instance, GAB-010 is highly selective to IRS1 but no binding to GAB1 or AKT1, largely due to the short $\beta_{1,2}$ loop. The knowledge that GAB1 PH domain undergoes conformational change upon ligand binding provides insights of guiding structure-based drug design efforts.

As used herein, the term "about" refers to plus or minus 10% of the referenced number.

The disclosures of the following U.S. Patents are incorporated in their entirety by reference herein: U.S. Pat. No. 8,420,678. Each reference cited in the present application is incorporated herein by reference in its entirety.

Various modifications of the invention, in addition to those described herein, will be apparent to those skilled in the art from the foregoing description. Such modifications are also intended to fall within the scope of the appended claims.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A compound of the formula III:

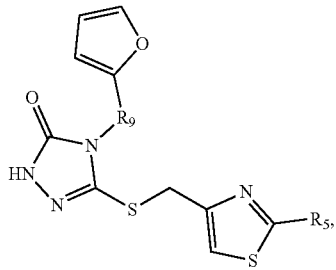

wherein $R_9$ is an alkylene, and wherein $R_5$ is a benzene, or a mono- or poly-substituted aryl group, or other aromatic heterocycle group.

2. The compound according to claim 1, wherein the compound is an inhibitor of Grb2-associated binder-1 (GAB1).

3. A pharmaceutical composition comprising a compound according to claim 1; and a pharmaceutically acceptable carrier or excipient.

4. The compound of claim 1, wherein the compound is:

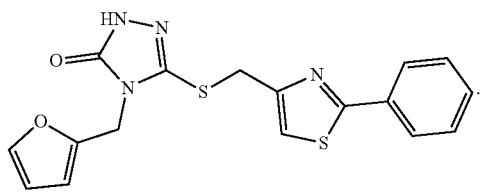 [SMILES: O=c1[nH]nc(SCc2csc(-c3ccccc3)n2)n1Cc1ccco1]

* * * * *

SEQUENCE LISTING

```
<160> NUMBER OF SEQ ID NOS: 5

<210> SEQ ID NO 1
<211> LENGTH: 112
<212> TYPE: PRT
<213> ORGANISM: Artificial Sequence
<220> FEATURE:
<223> OTHER INFORMATION: Grb2-associated binding protein 1 (GAB1), a
      protein coding gene

<400> SEQUENCE: 1

Glu Val Val Cys Ser Gly Trp Leu Arg Lys Ser Pro Pro Glu Lys Lys
1               5                   10                  15

Leu Lys Arg Tyr Ala Trp Lys Arg Arg Trp Phe Val Leu Arg Ser Gly
            20                  25                  30

Arg Leu Thr Gly Asp Pro Asp Val Leu Glu Tyr Tyr Lys Asn Asp His
        35                  40                  45

Ala Lys Lys Pro Ile Arg Ile Ile Asp Leu Asn Leu Cys Gln Gln Val
    50                  55                  60

Asp Ala Gly Leu Thr Phe Asn Lys Lys Glu Phe Glu Asn Ser Tyr Ile
65                  70                  75                  80

Phe Asp Ile Asn Thr Ile Asp Arg Ile Phe Tyr Leu Val Ala Asp Ser
                85                  90                  95

Glu Glu Glu Met Asn Lys Trp Val Arg Cys Ile Cys Asp Ile Cys Gly
            100                 105                 110

<210> SEQ ID NO 2
<211> LENGTH: 103
<212> TYPE: PRT
<213> ORGANISM: Artificial Sequence
<220> FEATURE:
<223> OTHER INFORMATION: Insulin Receptor Substrate 1 (IRS1), a protein
      coding gene, IQQG

<400> SEQUENCE: 2

Asp Val Arg Lys Val Gly Tyr Leu Arg Lys Pro Lys Ser Met His Lys
1               5                   10                  15

Arg Phe Phe Val Leu Arg Ala Ala Ser Glu Ala Gly Gly Pro Ala Arg
```

```
                20                  25                  30
Leu Glu Tyr Tyr Glu Asn Glu Lys Lys Trp Arg His Lys Ser Ser Ala
            35                  40                  45

Pro Lys Arg Ser Ile Pro Leu Glu Ser Cys Phe Asn Ile Asn Lys Arg
        50                  55                  60

Ala Asp Ser Lys Asn Lys His Leu Val Ala Leu Tyr Thr Arg Asp Glu
65                  70                  75                  80

His Phe Ala Ile Ala Ala Asp Ser Glu Ala Glu Gln Asp Ser Trp Tyr
                85                  90                  95

Gln Ala Leu Leu Gln Leu His
                100
```

<210> SEQ ID NO 3
<211> LENGTH: 101
<212> TYPE: PRT
<213> ORGANISM: Artificial Sequence
<220> FEATURE:
<223> OTHER INFORMATION: Tandem PH domain-containing protein 1 (TAPP1), an adapter protein, 1EAZ

<400> SEQUENCE: 3

```
Ala Val Ile Lys Ala Gly Tyr Cys Val Lys Gln Gly Ala Val Met Lys
1               5                   10                  15

Asn Trp Lys Arg Arg Tyr Phe Gln Leu Asp Glu Asn Thr Ile Gly Tyr
            20                  25                  30

Phe Lys Ser Glu Leu Glu Lys Glu Pro Leu Arg Val Ile Pro Leu Lys
        35                  40                  45

Glu Val His Lys Val Gln Glu Cys Lys Gln Ser Asp Ile Met Met Arg
    50                  55                  60

Asp Asn Leu Phe Glu Ile Val Thr Thr Ser Arg Thr Phe Tyr Val Gln
65                  70                  75                  80

Ala Asp Ser Pro Glu Glu Met His Ser Trp Ile Lys Ala Val Ser Gly
                85                  90                  95

Ala Ile Val Ala Gln
                100
```

<210> SEQ ID NO 4
<211> LENGTH: 99
<212> TYPE: PRT
<213> ORGANISM: Artificial Sequence
<220> FEATURE:
<223> OTHER INFORMATION: Myosin X , a protein coding gene, 3TFM

<400> SEQUENCE: 4

```
Glu Ala Leu Lys Gln Gly Trp Leu His Asn Asn Gly Gly Gly Ser Ser
1               5                   10                  15

Thr Leu Ser Arg Arg Asn Trp Lys Lys Arg Trp Phe Val Leu Arg Gln
            20                  25                  30

Ser Lys Leu Met Tyr Phe Glu Asn Asp Ser Glu Glu Lys Leu Lys Gly
        35                  40                  45

Thr Val Glu Val Arg Ser Ala Lys Glu Ile Ile Asp Asn Thr Asn Lys
    50                  55                  60

Glu Asn Gly Ile Asp Ile Ile Met Ala Asp Arg Thr Phe His Leu Ile
65                  70                  75                  80

Ala Glu Ser Pro Glu Asp Ala Ser Gln Trp Phe Ser Val Leu Ser Gln
                85                  90                  95

Val His Ser
```

```
<210> SEQ ID NO 5
<211> LENGTH: 97
<212> TYPE: PRT
<213> ORGANISM: Artificial Sequence
<220> FEATURE:
<223> OTHER INFORMATION: Dual Adaptor Of Phosphotyrosine And
      3-Phosphoinositides (DAPP1), a protein coding gene, 1FAO

<400> SEQUENCE: 5

Leu Gly Thr Lys Glu Gly Tyr Leu Thr Lys Gln Gly Gly Leu Val Lys
1               5                   10                  15

Thr Trp Lys Thr Arg Trp Phe Thr Leu His Arg Asn Glu Leu Lys Tyr
            20                  25                  30

Phe Lys Asp Gln Met Ser Pro Glu Pro Ile Arg Ile Leu Asp Leu Thr
        35                  40                  45

Glu Cys Ser Ala Val Gln Phe Asp Tyr Ser Gln Glu Arg Val Asn Cys
    50                  55                  60

Phe Cys Leu Val Phe Pro Phe Arg Thr Phe Tyr Leu Cys Ala Lys Thr
65                  70                  75                  80

Gly Val Glu Ala Asp Glu Trp Ile Lys Ile Leu Arg Trp Lys Leu Ser
                85                  90                  95

Gln
```